US011672680B2

(12) United States Patent
King et al.

(10) Patent No.: US 11,672,680 B2
(45) Date of Patent: Jun. 13, 2023

(54) GROWTH ADAPTIVE EXPANDABLE STENT

(71) Applicant: THE CHARLES STARK DRAPER LABORATORY, INC., Cambridge, MA (US)

(72) Inventors: Daniel F. King, Watertown, MA (US); Stephanie Lynne Golmon, Arlington, MA (US); Jonathan R. Coppeta, Windham, NH (US); Jesse M. Carr, Cambridge, MA (US); Corin Williams, Framingham, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 320 days.

(21) Appl. No.: 16/637,664

(22) PCT Filed: Aug. 10, 2018

(86) PCT No.: PCT/US2018/046309
§ 371 (c)(1),
(2) Date: Feb. 7, 2020

(87) PCT Pub. No.: WO2019/033026
PCT Pub. Date: Feb. 14, 2019

(65) Prior Publication Data
US 2021/0353443 A1   Nov. 18, 2021

Related U.S. Application Data

(60) Provisional application No. 62/684,464, filed on Jun. 13, 2018, provisional application No. 62/544,231, filed on Aug. 11, 2017.

(51) Int. Cl.
*A61F 2/89* (2013.01)
*A61F 2/24* (2006.01)
*A61F 2/82* (2013.01)

(52) U.S. Cl.
CPC .............. *A61F 2/89* (2013.01); *A61F 2/2418* (2013.01); *A61F 2002/825* (2013.01);
(Continued)

(58) Field of Classification Search
CPC .... A61F 2/89; A61F 2/2418; A61F 2002/825; A61F 2210/0014; A61F 2250/001; A61F 2250/0082; A61F 2/848
See application file for complete search history.

(56) References Cited

U.S. PATENT DOCUMENTS 6,159,239 A     12/2000  Greenhalgh
7,156,869 B1 *   1/2007  Pacetti ...................... A61F 2/91
                                              606/192
(Continued)

FOREIGN PATENT DOCUMENTS

EP          1958597 A1 *  8/2008   ................ C25F 3/22
EP          2311410 A1     4/2011
WO       2005122714 A2    12/2005

OTHER PUBLICATIONS

International Search Report and the Written Opinion of the International Searching Authority from corresponding PCT/US2018/046309 dated Oct. 22, 2018.

*Primary Examiner* — Leslie Lopez
(74) *Attorney, Agent, or Firm* — Foley & Lardner LLP

(57) ABSTRACT

According to various aspects and embodiments, a growth adaptive expandable stent is provided. The expandable stent includes a stent structure having a cylindrical shape that is self-expanding in a radial direction and includes a plurality of cylindrical rings disposed along a longitudinal axis of the stent structure. The stent structure is configured to exert a continuous outward radial force over time when implanted (Continued)

such that a diameter of the stent structure expands from a first value to a second value that is at least about 1.5 times the first value.

34 Claims, 17 Drawing Sheets

(52) U.S. Cl.
CPC . *A61F 2210/0014* (2013.01); *A61F 2250/001* (2013.01); *A61F 2250/0082* (2013.01)

(56) References Cited

U.S. PATENT DOCUMENTS

| | | | |
|---|---|---|---|
| 8,747,453 | B2 | 6/2014 | Amplatz et al. |
| 9,034,033 | B2* | 5/2015 | McLean ............... A61F 2/2445 |
| | | | 623/2.12 |
| 9,066,825 | B2 | 6/2015 | Chanduszko |
| 9,387,098 | B2* | 7/2016 | Ferrera ............ A61B 17/12118 |
| 2002/0128706 | A1* | 9/2002 | Osypka .................... A61F 2/92 |
| | | | 623/1.15 |
| 2003/0004536 | A1* | 1/2003 | Boylan ................. A61F 2/0108 |
| | | | 606/200 |
| 2004/0249446 | A1* | 12/2004 | Patel ......................... A61F 2/91 |
| | | | 623/1.16 |
| 2005/0137682 | A1 | 6/2005 | Justino |
| 2006/0020334 | A1* | 1/2006 | Lashinski ............... A61F 2/014 |
| | | | 623/2.11 |
| 2007/0150048 | A1 | 6/2007 | Tischler |
| 2008/0183273 | A1 | 7/2008 | Mesana et al. |
| 2011/0190872 | A1 | 8/2011 | Anukhin et al. |
| 2014/0296957 | A1 | 10/2014 | Janzten et al. |
| 2015/0080999 | A1 | 3/2015 | Zhao |
| 2015/0142103 | A1 | 5/2015 | Vidlund |
| 2015/0173898 | A1* | 6/2015 | Drasler ................. A61F 2/2433 |
| | | | 623/2.18 |
| 2016/0143755 | A1 | 5/2016 | Nishigishi |
| 2016/0220361 | A1 | 8/2016 | Weber et al. |
| 2016/0278922 | A1 | 9/2016 | Braido et al. |
| 2016/0338860 | A1 | 11/2016 | Sheldon et al. |
| 2016/0361159 | A1 | 12/2016 | Huber |
| 2017/0014228 | A1 | 1/2017 | Emani et al. |
| 2017/0035587 | A1 | 2/2017 | Kelly |
| 2017/0035588 | A1 | 2/2017 | Sheldon et al. |
| 2017/0065409 | A1 | 3/2017 | Scorsin et al. |
| 2017/0071766 | A1 | 3/2017 | During et al. |
| 2017/0165054 | A1 | 6/2017 | Benson et al. |
| 2017/0209268 | A1* | 7/2017 | Cunningham ............ A61F 2/95 |

* cited by examiner

GROWTH ADAPTIVE EXPANDABLE STENT

CROSS-REFERENCE TO RELATED APPLICATIONS

This application is a U.S. national phase application, and claims the benefit of priority under 35 U.S.C. § 371, of International (PCT) Patent Application Serial No. PCT/US2018/046309 titled "GROWTH ADAPTIVE EXPANDABLE STENT" filed Aug. 10, 2018, which claims priority under 35 U.S.C. § 119(e) to U.S. Provisional Application Ser. No. 62/544,231 titled "PEDIATRIC PROSTHETIC HEART VALVE DEVICE" filed Aug. 11, 2017, and to U.S. Provisional Application Ser. No. 62/684,464 titled "PEDIATRIC PROSTHETIC HEART VALVE DEVICE" filed Jun. 13, 2018, each of which is incorporated herein by reference in its entirety for all purposes.

BACKGROUND

Technical Field

The technical field relates generally to an expandable stent and, more specifically, to an expandable stent for use in heart valve devices, and, further, pediatric prosthetic heart valve devices.

Background Discussion

Typical prosthetic heart valve devices available on the market are constructed with geometries suitable for adults but are unsuitable for younger pediatric cardiac patients. Typical devices are either balloon expandable by plastic deformation or rely on shape memory properties for immediate expansion to a final diameter. Adult-sized replacement heart valves often have a fixed geometry that is too large for use in children, which requires surgeons to modify an adult-sized valve device to fit into a child, often in the operating room during surgery. This is a difficult and complicated procedure that is performed by only a few skilled surgeons. Furthermore, the devices do not have the ability to grow with the pediatric patient, thus requiring multiple invasive procedures or open heart surgeries. The lack of growth adaptation of current valve prosthetics is due to current stent designs relying on plastic deformation by balloon expansion or immediate self-expansion to a final diameter based on shape memory properties.

SUMMARY

The present disclosure introduces a third category of stent design: a tissue conformable, growth adaptive stent that utilizes super-elastic properties of materials to balance applied outward forces with tissue growth and deformation.

Aspects and embodiments are directed to a growth adaptive expandable stent for use in a heart valve device. According to one embodiment, a stent structure is provided having a cylindrical shape that is self-expanding in a radial direction, the stent structure having a proximal end portion, a distal end portion, and a central portion and comprising a plurality of cylindrical rings disposed along a longitudinal axis of the stent structure, each cylindrical ring of the plurality of cylindrical rings having a plurality of interconnected struts. The stent structure is configured to exert a chronic outward radial force over time when implanted such that an outer diameter of the stent structure expands from a first value to a second value that is at least about 1.5 times the first value.

In some embodiments, the chronic outward radial force is sufficient to allow the outer diameter of the stent structure to adapt to a natural growing shape of a biological feature in which the stent structure is implanted.

In some embodiments, the stent structure has a chronic outward radial force that decreases by up to 100% when the outer diameter expands from the first value to the second value. According to certain embodiments, the outer diameter has a first value in a range of about 4 millimeters to about 20 millimeters. According to another embodiment, the outer diameter has a first value that is in a range of about 5 millimeters to about 10 millimeters.

In accordance with at least one embodiment, the stent structure is configured such that a length of the stent structure remains substantially constant when the outer diameter of the stent structure expands from the first value to the second value.

In some embodiments, a ratio of a depth to a localized width of each strut allows for preferential bending. In some embodiments, the ratio of the depth of the strut to the localized width of the strut is greater than one. In some embodiments, the depth of the strut is in a range of about 50 microns to about 2000 microns.

In certain embodiments the length of the stent structure is in a range of about 7 millimeters to about 30 millimeters when the outer diameter is the second value.

In some embodiments, the length of the stent structure is configured to prevent ingrowth of a patient's tissue into the stent structure without disrupting or occluding blood flow. In some embodiments a ratio of the length of the stent structure to the outer diameter of the stent structure is at least one.

In some embodiments, the growth adaptive expandable stent includes a plurality of restraining structures that are disposed around a longitudinal axis of the stent structure. In some embodiments, each restraining structure includes at least one retaining feature. In some embodiments, each restraining structure has a first end portion and a second end portion, at least one of the first end portion and the second end portion including a retaining feature.

In some embodiments, at least one of the retaining features is a ring. In some embodiments, at least one of the retaining features is a nubbin.

In some embodiments, each of the restraining structures is interspersed with the plurality of cylindrical rings.

In some embodiments, the plurality of restraining structures are interspersed with the plurality of cylindrical rings such that a pair of restraining structures are separated from one another by segments of the plurality of cylindrical rings.

According to one embodiment, the plurality of interconnected struts are configured such that two adjacent struts are connected to each other at an apex.

According to another embodiment, the stent structure, and the plurality of restraining structures, are formed from a common source material. In some embodiments the common source material is formed of a bio-compatible super-elastic material.

In some embodiments, the stent structure is configured to support a valve assembly.

In accordance with at least one embodiment, the valve assembly has one or more leaflets and is secured to at least one of the stent structure and the plurality of restraining structures.

According to some embodiments, the stent structure and the plurality of restraining structures are configured for a pediatric patient.

According to some embodiments, the growth adaptive expandable stent further includes a sheath disposed on outer surfaces of the stent structure. In some embodiments, the expandable stent further includes a sheath disposed on outer surfaces of the stent structure and the plurality of restraining structures. In some embodiments, the expandable stent further includes a sheath disposed on inner surfaces of the stent structure and the plurality of restraining structures. In some embodiments, the expandable stent further includes a sheath that is flush with an outer surface of the stent structure and/or the plurality of restraining structures.

According to some embodiments, the expandable stent further comprises an annular cuff secured to at least a portion of the central portion of the stent structure.

In some embodiments, the outer diameter of the stent structure expands from the first value to the second value, and the second value is between about 1.5 times the first value and about 5 times the first value.

In some embodiments, the outer diameter of the stent structure expands from the first value to the second value, and the second value is between about 1.5 times the first value and about 3 times the first value.

In some embodiments, the outer diameter of the stent structure expands from the first value to the second value, and the second value is at least twice the first value. In some embodiments, the growth adaptive expandable stent further includes a plurality of restraining structures disposed around a circumferential axis of the stent structure and interspersed with the plurality of cylindrical rings of the stent structure. In some embodiments, the growth adaptive expandable stent further includes an annular cuff secured to at least a portion of the central portion of the stent structure. In some embodiments, the growth adaptive expandable stent includes a sheath disposed on outer surfaces of the stent structure.

Still other aspects, embodiments, and advantages of these example aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Embodiments disclosed herein may be combined with other embodiments, and references to "an embodiment," "an example," "some embodiments," "some examples," "an alternate embodiment," "various embodiments," "one embodiment," "at least one embodiment," "this and other embodiments," "certain embodiments," or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

Figure 1A:
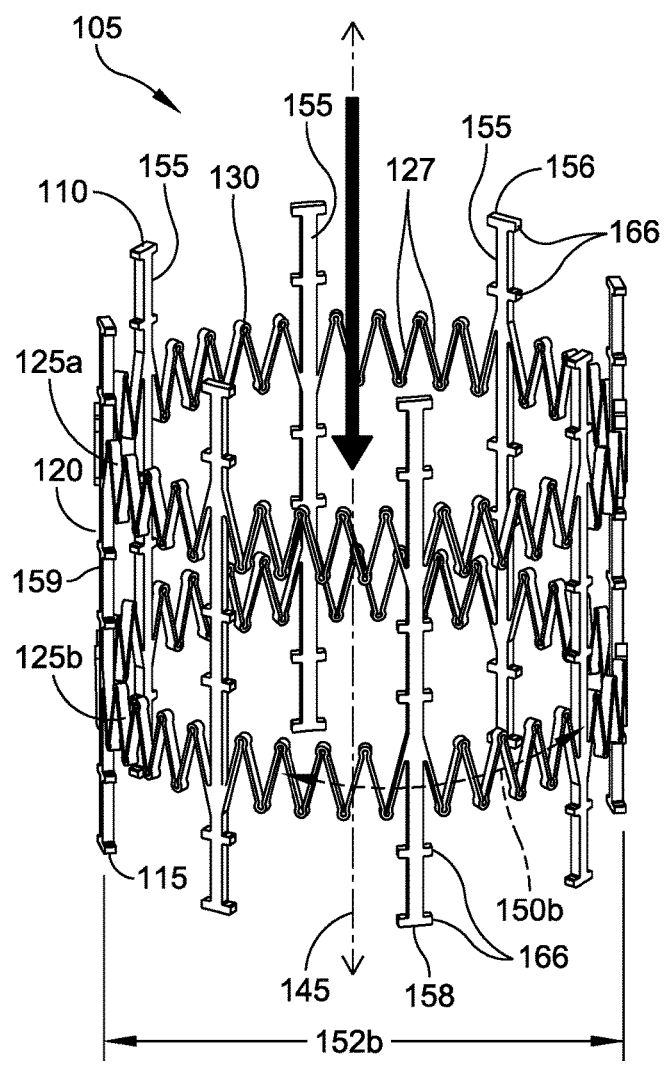
FIG. 1A is a perspective view of one example of a stent structure and a plurality of restraining structures, shown in an expanded state in accordance with one or more aspects of the invention.

Tubular prosthetic devices used to maintain, open, or dilate blood vessels or other biological lumens are generally referred to as stents. Stent constructions generally include cylindrical frames that define a plurality of openings. Stents can be classified into two broad classes: self-expanding stents and balloon expandable stents. Self-expanding stents typically expand to a final diameter in a short time frame once a constraining force is removed, such as an outer sheath of a stent delivery system. Self-expanding stents formed from shape-memory materials may also expand via a change in temperature. Self-expanding stents are generally loaded into a stent delivery system by collapsing the stent from an expanded configuration to a collapsed configuration. Balloon expandable stents rely on plastic deformation for expansion and are typically expanded via an inflation force, such as a balloon catheter. Balloon expandable stents are generally loaded onto a balloon catheter through a crimping process to transition the stent to a collapsed configuration, and are plastically deformed when the balloon is inflated in the blood vessel or other tissue lumen to the expanded configuration. Here we introduce a third category of stent design: a growth adaptive stent that conforms to the biological structure, such as a heart valve annulus, and expands as the tissue structure grows or changes shape. This adaptive stent design utilizes the super-elastic properties of its material rather than traditional plastic deformation of balloon expandable stents or shape memory properties of self-expanding stents.

As explained above, surgeons often must modify adult-sized heart valve replacement devices to fit young children. Typical devices are configured for fully grown organs and blood vessels, and therefore do not have sizes that are suitable for children and also fail to have growth-adaptive capabilities to accommodate somatic growth and hemodynamic changes as the child's heart grows. As a result, multiple open heart surgeries for implanting successively larger devices may be required, which is detrimental to the health of patients whose cardiac systems are already compromised. Typical devices also come in fixed diameters and thus may also fail to accommodate custom sizes necessary for adults. Furthermore, the transcatheter delivery systems and processes currently used for adults may be detrimental or physically impossible for use in the blood vessels of children, especially those under age 5-6.

The growth adaptive expandable stents disclosed and described herein are designed to address several of the problems highlighted above regarding the use of the stent with typical heart valve replacement devices. The growth adaptive expandable stents of this disclosure, for example, when used as part of a prosthetic heart valve device, are designed to enlarge passively as the patient grows, are optimized for the hemodynamics of a child, and may be small enough for use in infants born with heart defects. As well, these structures may provide a better custom fit for adult applications.

As described herein, the growth adaptive self-expanding stent of the present disclosure is capable of providing a chronic outward force that is sufficient to allow the outer diameter of the stent to adapt to a natural growing shape of a biological feature. In some embodiments, the biological feature is a blood vessel. In some embodiments, the biological feature is the annulus of a heart valve.

The growth adaptive expandable stents of this disclosure are growth adaptive self-expanding stent structures that do not require use of another device, such as a balloon, to expand after implantation. Additionally, the growth adaptive expandable stents of this disclosure are growth adaptive self-expanding stent structures that are configured to securely engage tissue in a patient as the stent expands itself from a first diameter (when the stent is implanted) to a second diameter over a period of time. In some embodiments, the period of time is at least one month. In some embodiments, the period of time is at least one year. In some embodiments, the period of time is at least five years. In some embodiments, the period of time is at least 10 years. In some embodiments, the period of time is sufficiently long that the patient may avoid a stent or valve replacement surgery that would otherwise be required if a typical non-adaptable stent or heart valve device had been used. In some embodiments, the growth adaptive self-expanding stent undergoes a gentle or gradual expansion so that the diameter of the growth adaptive self-expanding stent increases as the patient's valve or vessel diameter naturally increases. In some embodiments, the expansion of the growth adaptive self-expanding stent is enabled by forming the stent from an alloy or another material that has super-elastic material properties. The material of the growth adaptive self-expanding stent does not experience plastic deformation when the stent expands from a compressed diameter to its final diameter.

The growth adaptive self-expanding stents of the present disclosure are also useful in patients in which the heart and blood vessels have stopped growing. Typical stents used in heart valve replacement have standardized sizes. The standardized sizes differ in diameter by between 1 and 2 millimeters. The growth adaptive self-expanding stents of the present disclosure can be used in place of typical fixed diameter stents or devices to provide a customized conformable fit against the tissue of the patient when implanted without the need for multiple sizes on hand during surgery.

The aspects disclosed herein in accordance with the present invention, are not limited in their application to the details of construction and the arrangement of components set forth in the following description or illustrated in the accompanying drawings. These aspects are capable of assuming other embodiments and of being practiced or of being carried out in various ways. Examples of specific implementations are provided herein for illustrative purposes only and are not intended to be limiting. In particular, acts, components, elements, and features discussed in connection with any one or more embodiments are not intended to be excluded from a similar role in any other embodiments.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls. Moreover, titles or subtitles may be used in the specification for the convenience of a reader, which shall have no influence on the scope of the present invention.

FIG. 1A is a perspective view of a stent structure 105. The stent structure includes a plurality of restraining structures 155. As discussed further herein, such a stent structure 105 may be used in a prosthetic heart valve device. The stent structure 105 has a proximal end portion 110, a distal end portion 115, and a central portion 120, as well as a longitudinal axis 145, a circumferential axis 150 (marked as 150a in FIG. 1B and 150b in FIG. 1A), and a diameter 152 (shown in FIGS. 1A and 1B as 152a and 152b). As used herein, the diameter 152 of the stent structure 105 refers to the outer diameter.

Figure 1B:
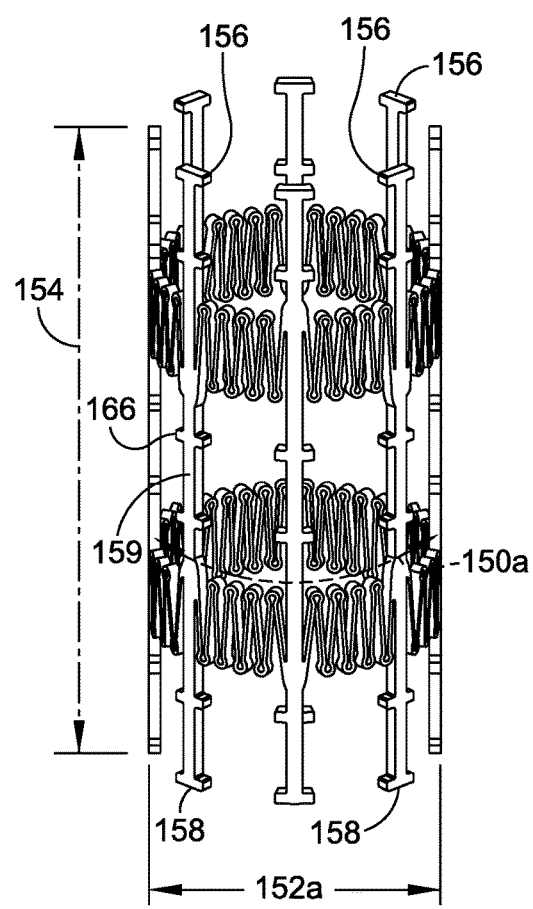
FIG. 1B is a perspective view of the stent structure and a plurality of restraining structures shown in FIG. 1A configured in an initial state in accordance with one or more aspects of the invention.

The stent structure 105 shown in FIG. 1A comprises a plurality of cylindrical rings 125 disposed along a longitudinal axis 145 of the stent structure 105. Each cylindrical ring 125 includes a plurality of interconnected struts 127. The struts may be configured such that two adjacent struts 127 are connected to each other at an apex 130. This type of structure allows the stent structure 105 to radially expand and contract as the struts 127 bend about the apex 130. For instance, the angle formed by the apex and adjoined struts can increase such that the stent structure 105 can expand outward. Two adjacent struts 127 may be substantially parallel to one another (i.e., the angle formed by the apex and the adjoining struts may be very small, such as less than 10°) when the device is in an initial state (for example, for delivery to the implantation site as described below) or in an initial state after being implanted, as is shown in FIG. 1B. This angle increases as the device expands and the adjacent struts move apart. The geometry of the apex 130 may be such that the apex forms a slightly rounded structure, as shown in FIGS. 1A and 1B.

According to one embodiment, multiple cylindrical rings 125 may be positioned along the longitudinal axis 145 of the stent. In some embodiments, the cylindrical rings 125 may be positioned in a predetermined pattern and/or may be positioned to achieve a desired flexibility to the overall stent. In accordance with various embodiments, the device includes at least two cylindrical rings 125 (with two cylindrical rings indicated at 125a and 125b). The embodiment shown in FIGS. 1A and 1B is one example of an arrangement where one cylindrical ring 125a is disposed at the proximal end portion 110 of the stent structure 105, and one cylindrical ring 125b is disposed at the distal end portion 115 of the stent structure 105. As illustrated in FIGS. 1A, and 1B, the cylindrical rings 125 are configured to divide the device into approximately three equal portions. Positioning the cylindrical rings apart from one another may also function to allow for easier handling by the surgeon during the implantation procedure. In addition, this positioning provides stability to the stent to avoid coning or barreling of the stent structure. It is to be appreciated that the particular arrangement shown in the accompanying figures is not limiting and other configurations for the cylindrical rings along the longitudinal axis 145 are within the scope of this disclosure. For instance, other configurations may include three or more separate rings spaced apart from one another. Depending on the desired design, the separate rings may be spaced evenly or unevenly from one another and may divide the device into approximately equal or unequal portions.

Generally speaking, the stent structure may include a pattern or network of cylindrical rings and interconnecting structural elements of struts, which may be arranged in different patterns or configurations. When the stent structure is used in a prosthetic heart valve, the struts are designed to contact or apply force to the natural tissue annulus of the heart valve. The particular example shown in FIGS. 1A and 1B includes cylindrical rings with interconnected struts that form a "zig-zag" pattern, but other patterns are within the scope of this disclosure. In some embodiments, the stent structure, including the strut patterns, may be any configuration for achieving the functional properties of the prosthetic heart valve replacement devices discussed herein. For instance, circumferential stent structures generally include a series of cylindrical rings, formed by a series of connected struts, which may be joined together by connecting elements or bridges along (parallel to) a longitudinal axis of the stent. The pattern of struts and connecting elements can be configured depending on the desired attributes of the device. For example, the pattern can be configured to enhance flexibility or bendability and/or to ensure uniform expansion and prevent shortening of the length of the stent structure during expansion.

In FIGS. 1A, and 1B, a plurality of restraining structures 155 may be disposed along the circumferential axis 150 of the stent structure 105, around a longitudinal axis of the stent structure. The restraining structures 155 may be interspersed with the cylindrical rings 125 of the stent structure 105. As shown in FIG. 1A, the restraining structures 155 may also be disposed around the longitudinal axis 145 of the stent structure 105. According to some embodiments, the plurality of restraining structures 155 may be evenly spaced around the longitudinal axis 145 (i.e., along the circumferential axis 150), such that each restraining structure 155 is spaced evenly from an adjacent restraining structure. However, other arrangements may include restraining structures that are spaced unevenly around the longitudinal axis. One or more struts 127 may be attached to a restraining structure 155 and, as shown in FIG. 1A, two adjacent struts 127 may be joined to one another by a restraining structure 155. The restraining structure 155 may therefore be interspersed with the cylindrical rings 125 such that two adjacent struts 127 are joined by a restraining structure 155. The restraining structures may be interspersed with the plurality of cylindrical rings such that a pair of restraining structures are separated from one another by segments of the plurality of cylindrical rings.

The restraining structures 155 may function to add structural integrity to the stent structure 105, and, in fact, in certain aspects may be considered to be part of the stent structure 105. For instance, when used with the stent structure in a prosthetic heart valve device, the valve assembly 170 (as shown, for example in FIGS. 3A, 3B, 6, and 7), may be attached to the stent structure 105 such that the valve assembly is coupled to one or more of the restraining structures 155. According to various aspects, the restraining structure 155 may be used to interconnect the plurality of cylindrical rings 125 (or other types of cylindrical structures) that form the stent structure 105. The restraining structures 155 may be made from the same material as the stent structure 105, including the super-elastic materials. In some embodiments, the stent structure 105 and the restraining structures 155 may be formed from a single piece of tubing or from a common source material. The placement of the restraining structures 155 in relationship with the stent structure 105 may be configured to enhance or otherwise implement the desired outward radial force exerted by the stent structure 105 when expanding from the initial implanted state to the expanded state. In some embodiments the common source material is formed of a bio-compatible super-elastic material.

According to one embodiment, and as shown in FIGS. 1A and 1B, each restraining structure 155 has a first end portion 156, a second end portion 158, and a central portion 159. The first end portion 156 and the second end portion 158 extend from one another such that the restraining structure 155 is parallel to the longitudinal axis 145 of the stent structure 105. At least one retaining element (or retaining feature) 166, which may also be referred to herein as a retention element or a "retention nubbin," may be disposed on each restraining structure 155. For instance, the example shown in FIG. 1A has at least one retaining element 166 disposed on the first end portion 156, the second end portion 158, and the central portion 159. The retaining elements 166 may be evenly or unevenly spaced from one another along the length of the restraining structure 155. The embodiment shown in FIG. 1A includes two retaining elements 166 at each location, but it is to be appreciated that other embodiments may include one or three or more retaining elements 166 at various locations on the restraining structure 155.

The retaining element 166 functions to anchor any sutures, staples, or other attachment mechanisms used in attaching the valve in the device without having to pass a needle through a ring or other enclosed structure. In addition, the retaining element 166 may be used to attach an annular cuff 165 and/or sheath 168 (both described and shown below in FIGS. 5, 6, and 7). Positioning the retaining element 166 at the ends of the restraining structure 155 may also reduce the risk of puncturing tissue in comparison to other types of structures, due to its larger surface area.

Figure 6:
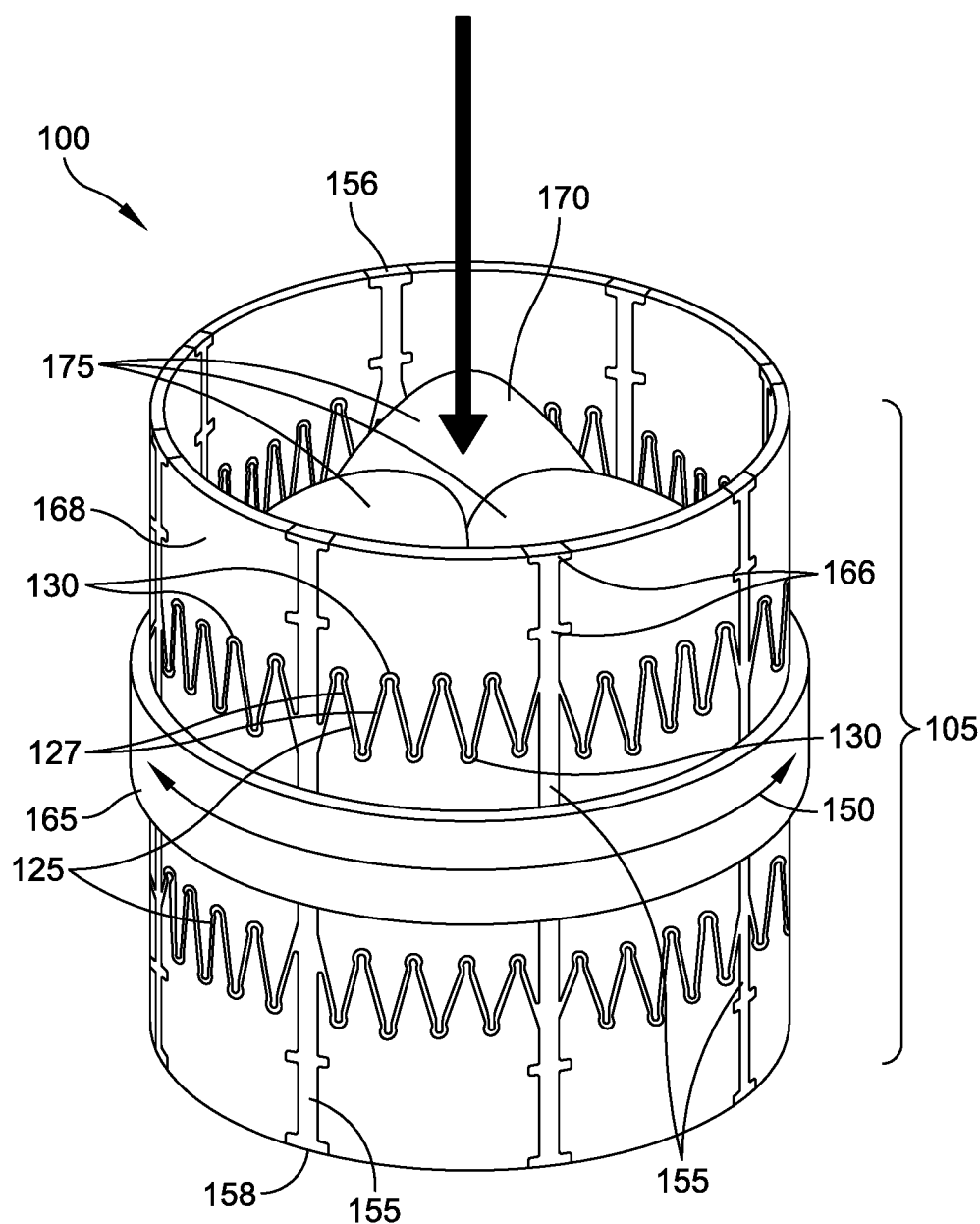
FIG. 6 is a perspective view of one example of a prosthetic heart valve device in accordance with one or more aspects of the invention.

The example shown in FIG. 6 has the retaining element 166 configured as a lateral expansion or extension off the restraining structure 155 and includes two retaining elements positioned such that they form an "I" shaped configuration in combination with the restraining structure 155, but other shapes and configurations are within the scope of this disclosure. According to one embodiment, the retaining elements 166 positioned at each of the first and second end portions 156 and 158 and the central portion 159 may be spaced at a distance in a range of between about 2.0 to about 2.5 millimeters from one another. The retaining element 166 may be sized large enough to allow for suture material of a desired gauge to "grab" onto during the attachment process. For instance, according to some embodiments, the retaining elements 166 may be sized to accommodate suture material having a gauge of from about United States Pharmacopeia (USP) gauge #6-0 to about #10-0.

Figure 2A:
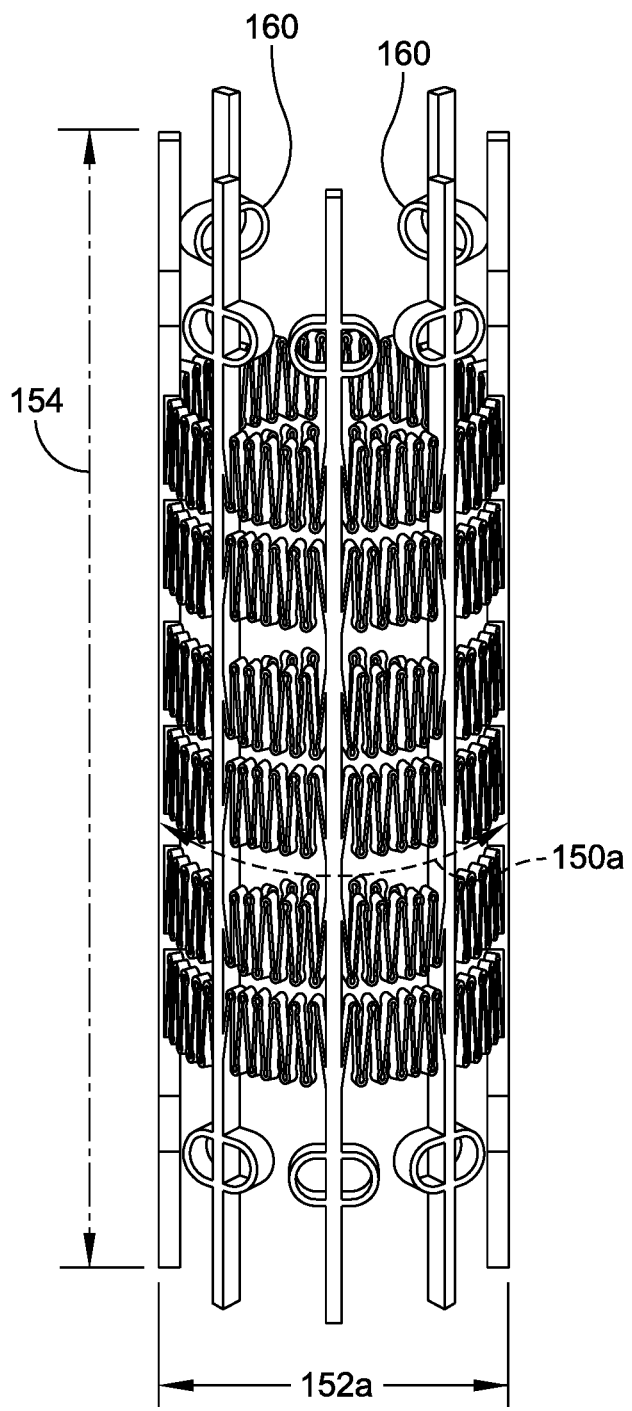
FIG. 2A is a perspective view of one example of an expandable stent in an initial state.
Figure 2B:
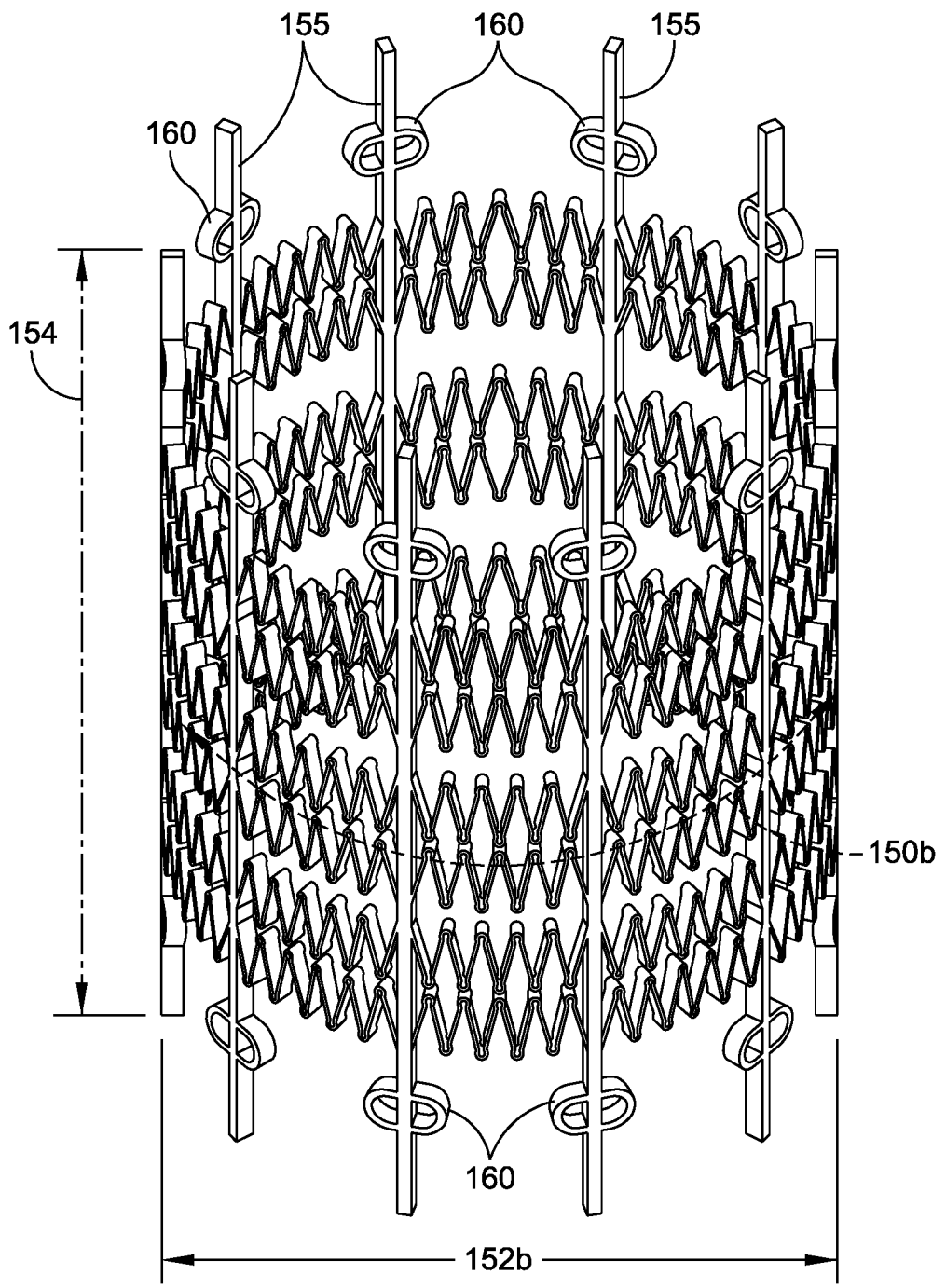
FIG. 2B is a perspective view of the expandable stent of FIG. 2A in an expanded state.
Figure 3A:
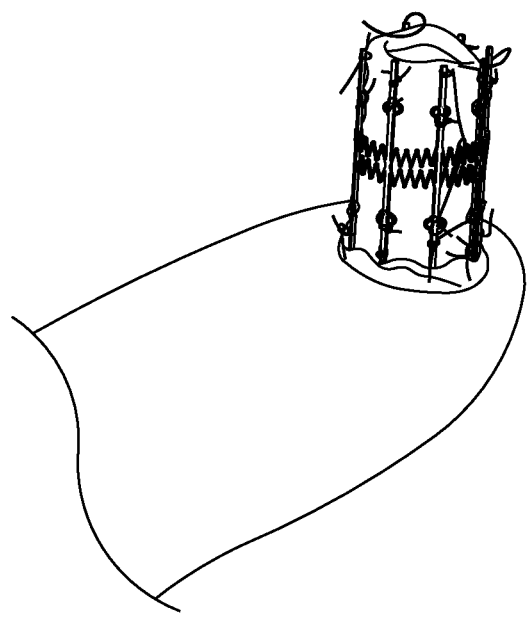
FIG. 3A is a view of another example of an expandable stent used in a prosthetic heart valve device in accordance with one or more aspects of the invention.
Figure 3B:
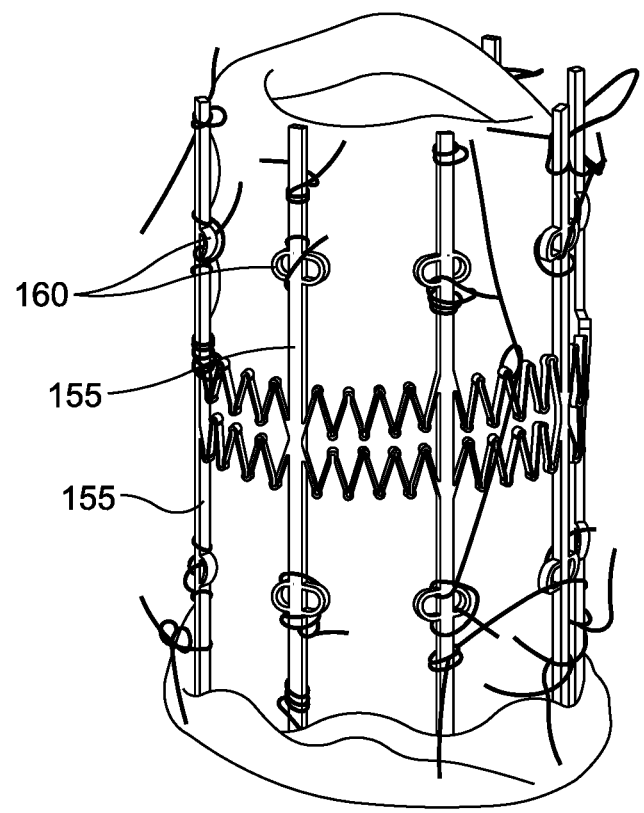
FIG. 3B is an enlarged view of the device shown in FIG. 3A.
Figure 4A:
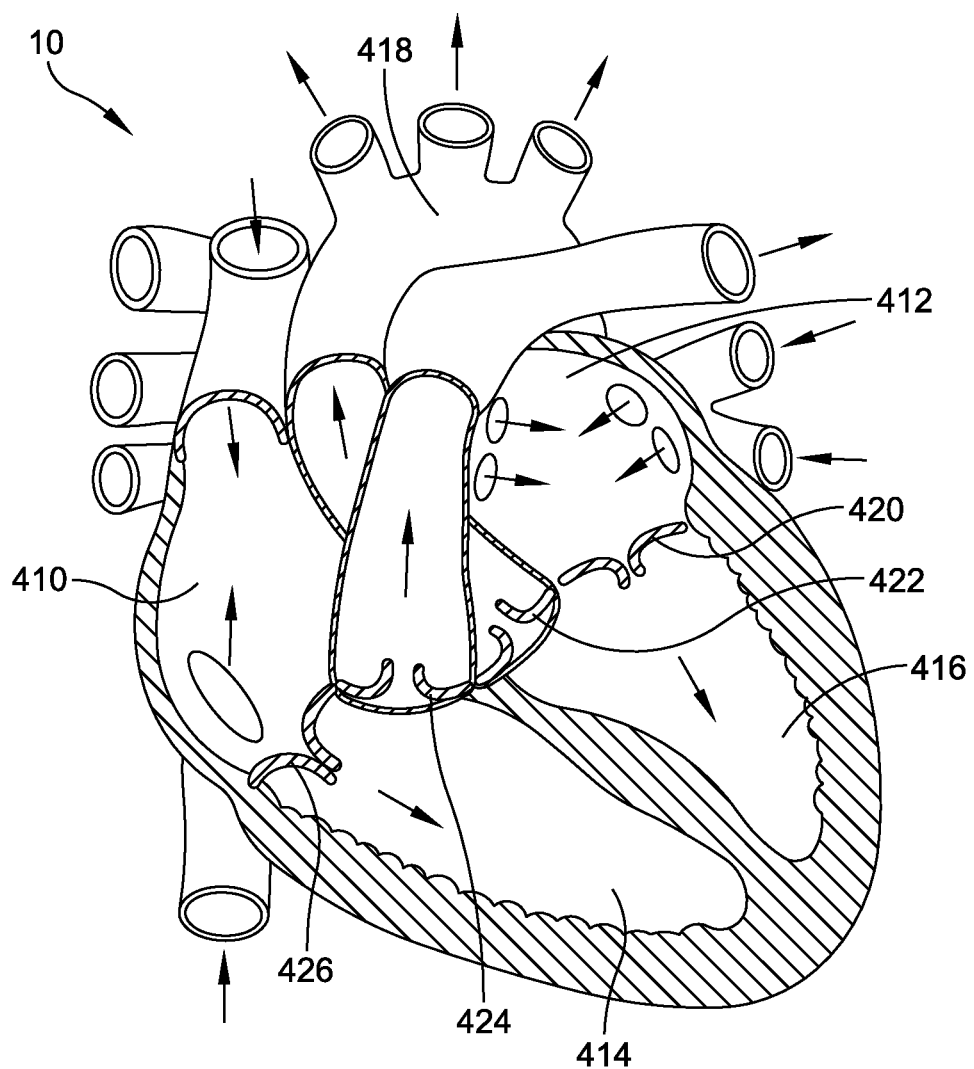
FIG. 4A is a schematic representation of a human heart showing locations where a prosthetic heart valve device may be positioned in accordance with one or more aspects of the invention.

According to some embodiments, each restraining structure 155 may include at least one retaining feature. According to some embodiments, each restraining structure 155 may include at least one retaining feature that is a suture ring 160. Suture rings are a type of retaining feature that may be used in place of nubbins, which are another type of retaining feature. FIGS. 2A and 2B show an embodiment of an expandable stent structure that includes suture rings disposed on the restraining structure. FIGS. 3A and 3B show another example of a growth adaptive expandable stent that is utilized as a prosthetic heart valve device, and that includes suture rings 160 disposed on the restraining structure 155. FIG. 4A is a schematic representation of a heart 10. As shown in FIG. 4A, the heart includes two atria and two ventricles: a right atrium 410 and a left atrium 412, and a right ventricle 414 and a left ventricle 416. The heart 10 also includes an aorta 418. Disposed between the left atrium 412 and the left ventricle 416 is the mitral valve 420, which is a dual-flap (two leaflet) valve that opens as a result of increased pressure in the left atrium as it fills with blood. As atrial pressure increases, the mitral valve opens and blood passes into the left ventricle in the direction indicated by the arrow shown in FIG. 4A. The aortic valve 422 has three leaflets and functions to maintain unidirectional blood flow between the left ventricle and the aorta. The aortic valve is effectively a one-way valve between the heart and the rest of the body since blood is pumped from the left ventricle, through the aortic valve, and into the aorta, which in turn supplies blood to all of the organs in the body. The pulmonary valve 424 is also a three leaflet valve and is positioned between the right ventricle and the pulmonary artery, which transports deoxygenated blood to the lungs from the heart. The tricuspid valve 426 is a three leaflet valve that forms the boundary between the right atrium and the right ventricle and functions to prevent back flow of blood into the right atrium.

Problems may occur with any one or more of the heart valves discussed above in human patients, especially in children. For instance, heart valve disease or congenital birth defects may cause the valve to function improperly or inadequately, such as by having holes or leaking, or the valve may be too narrow or completely closed. When this happens, a prosthetic heart valve device may be implanted into the patient to replace the defective valve. The prosthetic heart valves described below may be used to replace any one or more of the native heart valves shown in FIG. 4A.

Figure 4B:
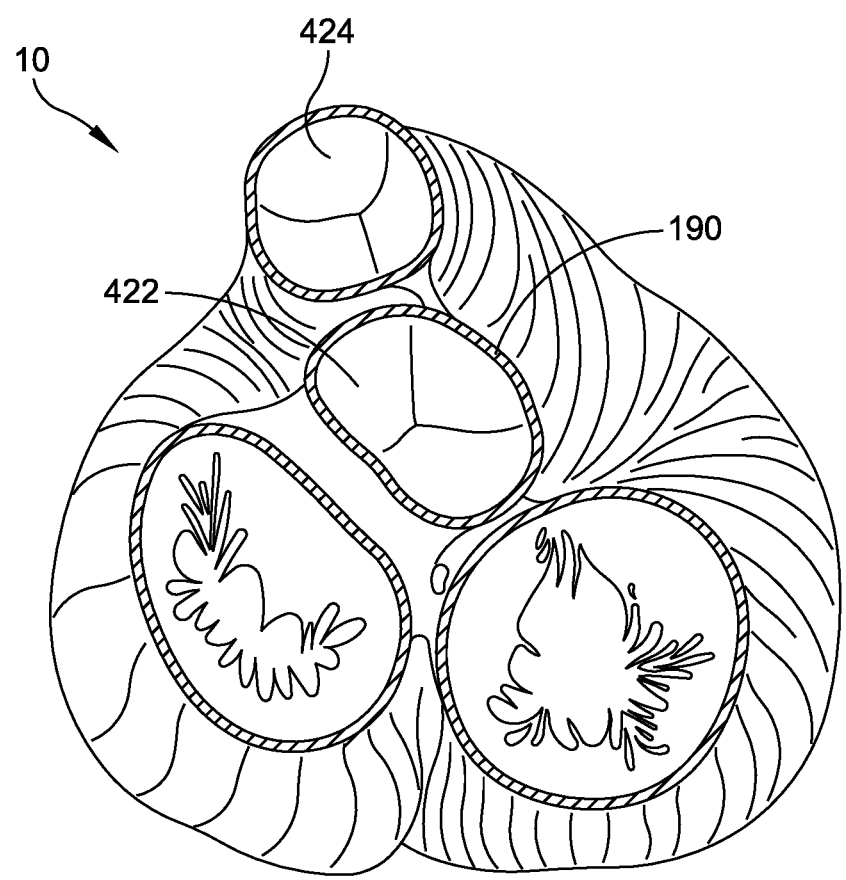
FIG. 4B is a cross-sectional view of the heart in a plane with the valves, showing the anatomical location of the valves relative to each other.

FIG. 4B shows a cross section of the heart in a plane with the valves, showing the anatomical location of the valves relative to each other. The annulus 190 is the "ring" of tissue around the valve where the leaflets in the respective valve attach. The annulus 190 may be the ring of tissue around any of the valves discussed in FIG. 4A. In some embodiments, the annulus may be a ring of tissue in a blood vessel.

Figure 5:
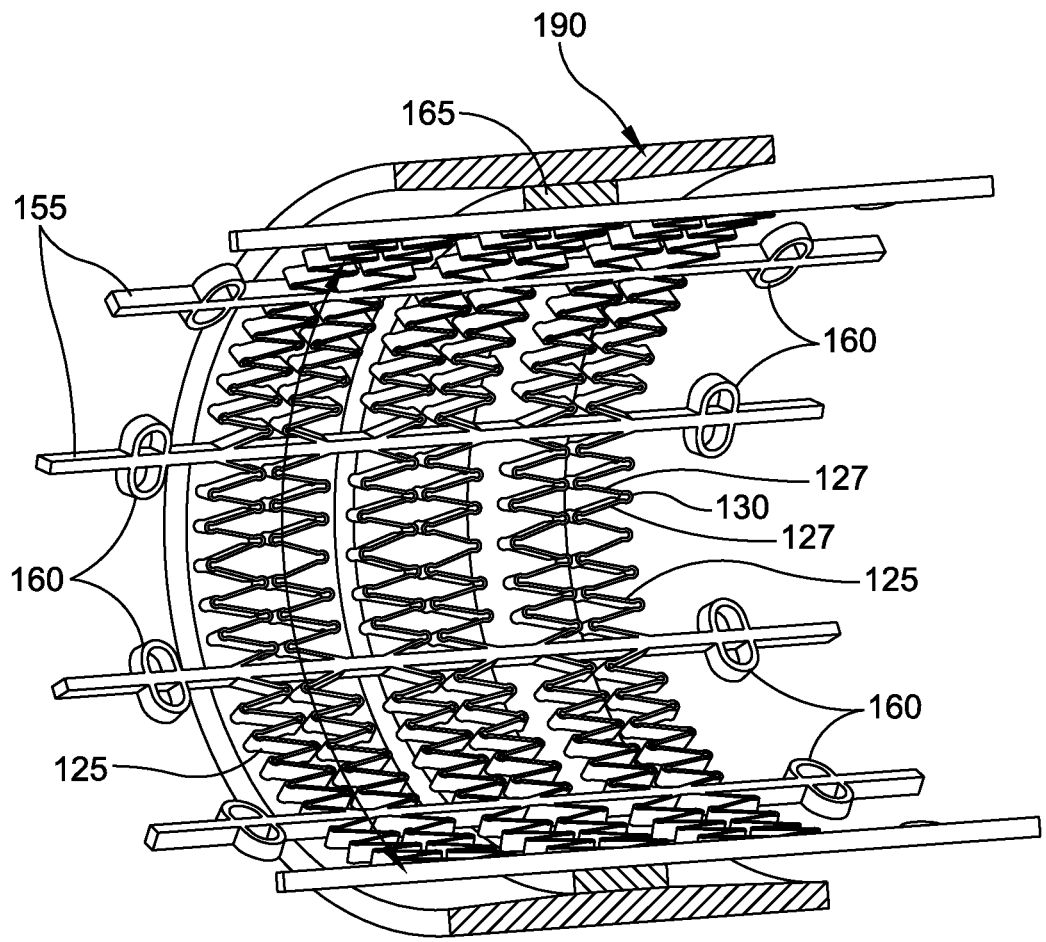
FIG. 5 is a cross-sectional view of a portion of one embodiment of a prosthetic heart valve device positioned within valve location of a heart in accordance with one or more aspects of the invention.

FIG. 5 is a cross-sectional view of a schematic of the stent structure 105 and restraining structures 155 of the device 100 shown in FIGS. 2A and 2B (described below) implanted in a patient's natural tissue annulus 190. Once implanted, a doctor may remove a constraining structure used to deliver the device to the implantation site and the stent will then begin applying force against the annulus 190. The stent will continue to slowly expand until it achieves a zero-stressed state at the desired maximum expanded diameter. In some embodiments, the growth adaptive stent continues to slowly expand until the chronic outward force (COF) is balanced by a resistive force of the tissue against the growth adaptive stent at that point in time. According to one aspect, a surgeon may attach one or more of the suture rings 160 of the restraining structures 155 to a portion of the native anatomy, such as a ventricle, for purposes of anchoring the device. The stent structure shown in FIG. 5 also includes an annular cuff 165. The cuff may be used to secure to at least a part of the central portion of the stent structure. As well, the cuff 165 may be used to secure the stent structure to the annulus 190.

FIG. 6 is a perspective view of one example of a prosthetic heart valve device (also referred to herein generally as "device"), shown generally at 100. As shown, the device 100 includes the stent structure 105 and the restraining structures 155 with retaining elements 166. Like the stent structure it includes the prosthetic heart valve device 100 and is configured to be self-expanding in a radial direction such that the device expands with the growth of a child or accommodating to various sized adults.

The prosthetic heart valve device 100 also includes a valve assembly 170 that is disposed within the stent structure 105 and has one or more leaflets 175 configured to permit blood flow in a first direction (as shown by arrow)) from an inflow end to an outflow end, and to impede blood flow in a second opposite direction. The valve assembly may be secured to the stent structure and/or the plurality of restraining structures.

Also included in the embodiment shown in FIG. 6, the prosthetic valve device may also include an annular cuff 165, which may also be referred to as a "suture skirt." The annular cuff 165 may be secured to at least a portion of the stent structure 105 and/or restraining structures 155 and may be placed around an outer edge of the stent. For instance, the annular cuff 165 may be attached to one or more struts 127 and/or restraining structures 155. The example shown in FIG. 6 is an example where the annular cuff 165 is attached to the restraining structures 155. The annular cuff 165 may be located in a central portion, e.g., the middle third, of the stent. In various embodiments, the annular cuff may be secured to at least a portion of the central portion of the stent structure. According to various aspects, the annular cuff 165 functions to ease handling of the device by doctors. For instance, the annular cuff 165 may make it easier for surgeons to move and position the device and secure it in place (i.e., by providing ready-made attachment points). The annular cuff 165 may be attached to the stent structure or restraining structures using any one of a variety of techniques. For instance, the annular cuff 165 may be attached using sutures, a biocompatible adhesive, or any other attachment method that does not interfere with the function and operation of the implanted device.

According to some embodiments, the annular cuff 165 may be constructed from the same material or materials as the stent structure 105 and the restraining structures 155. In some embodiments, the annular cuff may be constructed from a suitable synthetic material such as GORE-TEX® (W. L. Gore and Associates, Inc.). In certain embodiments, the annular cuff 165 may be formed from a biocompatible polymer material. Non-limiting examples of suitable materials include pericardium, biocompatible polymers, compliant polyurethanes, etc. In some embodiments, the annular cuff 165 may be constructed from a conformable material, and in other embodiments the annular cuff 165 may be constructed from a non-conformable material that is pleated to allow for expansion.

Referring to FIG. 6, in some embodiments the prosthetic heart valve replacement device 100 also includes a sheath 168 (which may also be referred to as an "external sheath") that functions to sheath the device, including the stent structure 105 and restraining structures 155, to protect the device from tissue ingrowth. The sheath 168 may be disposed on one or more outer surfaces of the stent structure 105 and/or restraining structures 155. The sheath 168 may be constructed from an elastomeric material, or from a suitable biocompatible material that is pleated or otherwise configured to allow for expansion. In some embodiments, the sheath is a thin coating. According to some embodiments, the sheath 168 is constructed from a bioprosthetic vein, biocompatible elastomer material, or pleatable biocompatible material. Non-limiting examples of biocompatible elastomer material include silicones and urethanes, such as THORALON® (Thoratec Corporation, Pleasanton, Calif.), and other suitable materials. In certain embodiments the sheath 168 may include two layers, one on an outer surface of the stent structure 105 and restraining structures 155 (but underneath the annular cuff 165), and one on an inner surface.

According to one embodiment, the stent structure 105 has a cylindrical shape and may be configured to bend in the circumferential direction to avoid buckling. The stent structure 105 is also self-expanding in a radial direction and is configured to support the valve assembly 170. Growth adaptive self-expanding stents may wholly or partly be formed of any non-biodegradable and biocompatible elastic material that acts like a spring and is capable of functioning as a stent as characterized herein. Non-limiting examples of materials that may be used to form the stent structure include biopolymers, metals, and synthetic polymers. Some examples of biopolymer materials include elastin and mixtures or composites thereof. Non-limiting examples of metal materials include cobalt, titanium, nickel, chromium, stainless steel, and alloys thereof. Non-limiting examples of synthetic polymers include thermoplastics, such as polyolefins, polyesters, polyamides, polysulfones, acrylics, polyacrylonitriles, polyetheretherketone (PEEK), and polyaramides.

In accordance with at least one embodiment, the stent material may be formed from a biocompatible super-elastic material. As used herein, the term "super-elastic material" broadly refers to any metal, metal alloy, plastic, or composite material that exhibits the ability to return to its original shape after severe deformations. According to one embodiment, the super-elastic material is a Nitinol alloy (made from nickel and titanium), which has the ability to return to its original dimensions when it is stretched up to or more than 10% of its original dimensions. Nitinol is a common biocompatible material, often utilized for its shape memory properties.

According to some embodiments, the stent material is made from a shape-memory alloy, which, after an apparent applied deformation, the material possesses the ability to recover its original shape upon heating or a reduction in stress due to a reversible solid-state phase transformation.

In some embodiments, the stent structure 105 may be formed from a super elastic material that undergoes substantially elastic deformation in expanding from an initial state or position to a fully expanded state or position. According to at least one embodiment, the stent structure 105 expands from an initial diameter (which refers to the outer diameter of stent structure 105) after implantation to a fully expanded position by stored energy. For instance, stored elastic energy of the self-expanding stent structure 105 can generate an outward or radially expansive force generally referred to as chronic outward force (COF) (also referred to herein as continuous outward radial force, or a chronic outward radial force). As used herein, COF refers to the continuing radial opening force of a self-expanding stent structure acting on a vessel wall or other tissue structure after having reached equilibrium against the tissue. COF may be expressed in units of force per unit length (e.g., Newtons/millimeter). According to some embodiments, the COF of the stent structure may be less than approximately 0.2 Newtons/millimeter, but smaller and larger values are also within the scope of this disclosure.

The COF of the stent structure 105 may be low enough such that it does not burst or damage the annulus or vessel wall. It will be recognized that when implanted, the stent structure may be in an initial compressed condition. In this initial state, the stent structure 105 is sized and shaped in accordance with the expected anatomy such that the stent structure 105 intimately contacts the native anatomy at a level of expansion less than a fully expanded condition. The chronic outward force supplied by the material and geometry of the stent structure 105 ensures that the stent structure securely lodges or anchors against the native anatomy while also applying a radial force onto the native anatomy to accommodate the growth of, for example, a pediatric patient.

In accordance with certain aspects, the stent structure 105 may also be capable of withstanding structural loads, for example radial compressive forces, imposed on the stent as it supports the walls of a vessel or annulus after implantation. Therefore, the stent structure 105 may exhibit adequate radial strength or resistance to radial compression, which is generally referred to as radial resistive force (RRF). As used herein, RRF refers to the force generated by the growth adaptive self-expanding stent structure 105 to resist compression, or the force required to compress the stent structure. RRF may also be expressed in units of force per unit length (e.g., Newtons/millimeter). The stent structure 105 can be configured such that the RRF is high enough to resist compression forces from the surrounding anatomical environment while still maintaining blood flow.

The prosthetic heart valve devices as disclosed herein are configured to balance forces between tissue growth and expansion. For instance, the prosthetic device is constructed from super-elastic materials and configured so that the structures have enough stored energy to continuously expand from an initial diameter to a fully expanded diameter over time. The device is therefore capable of growing with a child or a young adult, and accommodating various sized adults. In some embodiments, the expandable stent is capable of growing with an infant to adulthood. Many prosthetic heart valve devices are designed or constructed from materials that expand immediately from an initial compressed state but then stop expanding once the material contacts the walls of the heart anatomy. The balance of forces between the growth adaptive expanding stent of this invention and the constricting natural tissue annulus is such that the stent remains in contact with the annulus and/or forces the annulus to grow in diameter to a desired maximum value slowly over time. The device may be capable of inducing growth of the valve annulus of the patient. This capability addresses a problem with pediatric cardiac patients, for example, who may be forced to wait until they grow enough to accept an adult-sized replacement valve. However, the child's heart condition is often such that their physique, including their heart, does not grow at the normal rate because of the defective valve, thus creating a problematic situation. The devices disclosed herein allow for a patient to receive the device sooner. These devices also possess the ability to expand radially to accommodate and induce growth of the pediatric patient, particularly those who may have a tendency to form scar tissue.

Figure 7:
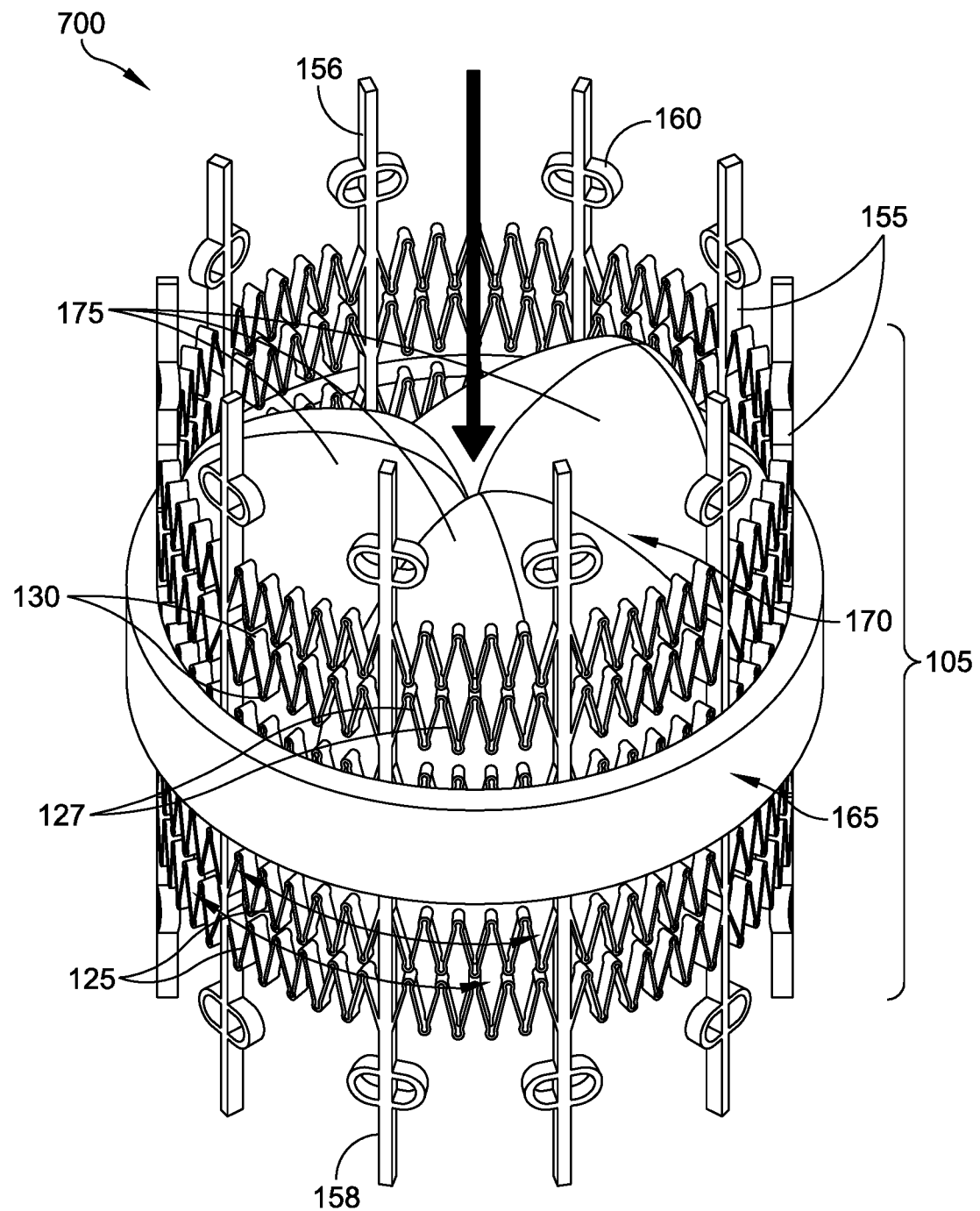
FIG. 7 is a perspective view of another example of a prosthetic heart valve device in accordance with one or more aspects of the invention.

FIG. 7 is a perspective view of another example of a prosthetic heart valve device, shown generally at 700, in accordance with one embodiment of the present disclosure. The prosthetic heart valve device 700 is configured to be self-expanding in a radial direction such that the device expands with the growth or size of the patient.

The prosthetic heart valve device 700 includes a stent structure 105, a plurality of restraining structures 155, and an annular cuff 165. The prosthetic heart valve device 700 also includes a valve assembly 170 that is disposed within the stent structure 105 and has one or more leaflets 175 configured to permit blood flow in a first direction (as shown by arrow) from an inflow end to an outflow end, and to impede blood flow in a second opposite direction.

At least one of the first end portion 156 and the second end portion 158 of each restraining structure 155 may include a suture ring 160. For instance, the embodiment shown in FIG. 7 includes a suture ring 160 at both the first end portion 156 and the second end portion 158.

Figure 8:
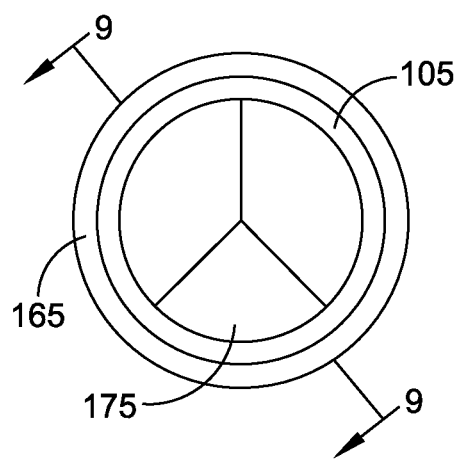
FIG. 8 is a plan schematic view of a prosthetic heart valve device in accordance with one or more aspects of the invention.
Figure 9:
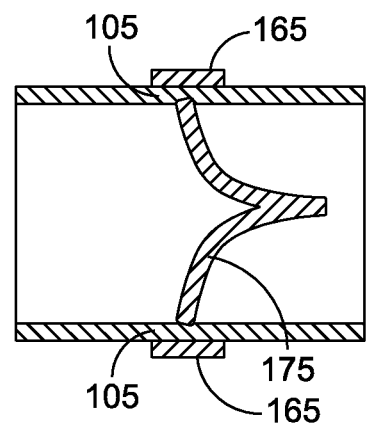
FIG. 9 is a cross-sectional side view taken along line 9-9 of the prosthetic heart valve device of FIG. 8.

FIG. 8 is a schematic plan view of the prosthetic heart valve device 100, and FIG. 9 is a cross-sectional view taken along line 9-9 of FIG. 8. FIGS. 8 and 9 show the annular cuff 165 disposed on the outer circumference of the stent structure 105 and restraining structures 155, as well as the leaflets 175 of the valve assembly. In some embodiments, the ratio of stent thickness to the diameter of the lumen in the tissue is less than about 10%. In some embodiments, the ratio of stent thickness to the diameter of the lumen in the tissue is less than about 7.5%. In some embodiments, the ratio of stent thickness to the diameter of the lumen in the tissue is less than about 5%. In some embodiments, the ratio of stent thickness to the diameter of the lumen in the tissue is less than about 2.5%. In some embodiments, the ratio of stent thickness to the diameter of the lumen in the tissue is about 1%.

Referring back to the structure of FIG. 1A and FIG. 1B, in accordance with various aspects, when used in a prosthetic heart valve device, the retention elements 166 may function to hold the device in a compressed state until it is implanted. For example, in certain embodiments the prosthetic heart valve device 100, including the stent structure 105 and restraining structures 155, is collapsible. These structures may be collapsible such that they are capable of being compressed for purposes of transcatheter implantation (described below) as well as implantation in the compressed state. According to some embodiments, the stent structure 105 and restraining structures 155 may be compressed to a diameter that is less than 5 millimeters, and in one embodiment, the stent may be compressed to a diameter of approximately 4 millimeters.

The retention elements 166 may be tied to one another using a securing material, such as a suture, or any other kind of suitable temporary fastening material or mechanism to hold the structure in the compressed state until the device is delivered to the desired implantation site. Once delivered, the securing material between the retention elements 166 may be cut, thus allowing the device to expand to an initial state. The securing material may be directly engaging the retention elements 166. In some embodiments in which suture rings are used, the securing material may be tied through and/or around the suture rings. In some embodiments, the securing material may be around other parts of the restraining structures 155.

According to another aspect, the retention elements 166 may function to prevent the prosthetic heart valve device from over-expanding. For instance, sutures or other suitable securing material may be attached to each of the retention elements 166 to interconnect them such that when the device radially expands the fibers become taut at a predetermined diameter; thereby preventing the device from exceeding the predetermined diameter.

To facilitate stent implantation, growth adaptive self-expanding stents may be installed on the end of a delivery catheter in a low profile, compressed state. The stent may be inserted into a sheath at the end of the catheter, which restrains the stent in the compressed state. The stent and catheter assembly, for example, may then be guided along a guide wire to the portion of the heart to be treated using the Seldinger technique, which is well known in the art. The ability of the stent to expand from a compressed diameter makes it possible to thread the stent through narrow, tortuous passageways to the area to be treated while the stent is in a relatively small, compressed diameter. Once the catheter and stent are positioned adjacent the portion of the heart or vessel to be treated, the stent is released by pulling, or withdrawing, the sheath rearward. Normally, a stop or other feature is provided on the catheter to prevent the stent from moving rearward with the sheath. After the stent is released from the retaining sheath, the stent may expand radially outward to an initial implanted diameter where the stent contacts and exerts force against the wall of the tissue. In some embodiments, growth adaptive stent structures are configured for use in open heart surgery for young patients. Some smaller embodiments of the growth adaptive stent structures are configured for use in open heart surgery. Some larger embodiments of the growth adaptive stent structures are configured for transcatheter procedures.

Once implanted, a surgeon or other clinician may remove the constraining structure used to deliver the device to the implantation site (or optionally the constraining structure may biodegrade) and the stent will then begin exerting force against the annulus. In some embodiments, the stent will continue to slowly expand until it nears the zero-stressed state, and is constrained by the inner diameter of a lumen in which it is implanted. In some embodiments, the stent will continue to slowly expand until it returns to the zero-stressed state at the desired maximum expanded diameter. According to one aspect, a surgeon may attach one or more of the retaining elements 166 to a portion of the native anatomy, such as a ventricle, for purposes of anchoring the device.

During heart surgery a patient's chest cavity is opened and blood is rerouted to a heart-lung bypass machine. Typically, the left or right atrium is opened to allow access to the heart chambers and valves that are in need of repair or replacement (mitral and aortic valves on the left side of the heart, tricuspid and pulmonary valves on the right). Prior to implanting the device, the surgeon may remove damaged valve tissue or expand the native valve annulus. The heart valve device may be placed into position via these surgical incisions into the heart and would be constrained to a diameter at or smaller than its initial intended state via a suture line or other constraining material through the retaining elements 166. The annular cuff 165 may facilitate suturing of the compressed device into the patient's heart valve annulus. Once the device is sutured in place within the annulus, the constraining material would be released, allowing the device to expand against the tissue but without significantly disrupting or deforming it. The tissue would then provide the constraining force necessary to prevent the stent from reaching its fully expanded diameter immediately after implantation.

According to at least one embodiment, the device is constrained to an implantation diameter using biodegradable sutures or sheaths. Once the biodegradable material decomposes, the device can expand against the tissue using stored energy as described herein. Using biodegradable materials allows for the patient to heal from surgery before the chronic outward force is applied against the annulus.

According to some embodiments the implantation process may be configured to be customized for each patient. For instance, an iris type mechanism (also referred to as a crimping iris) may be used to custom fit the device to an individual patient's required initial diameter. In a first step, the profile of the device is crimped down to specified dimensions using an iris type mechanism. Removable restraints, such as biodegradable material as described above, may be applied to the device prior to implantation.

As noted above, the stent structure 105 is capable of exerting a continuous outward radial force after initial implantation so as to allow the structure to further enlarge over time. For instance, according to one embodiment, the stent structure 105 is configured to exert a continuous outward radial force over time such that a diameter of the stent structure expands from a first value to a second value. FIG. 1B illustrates the stent structure and plurality of restraining structures at an initial implanted state where the circumferential axis 150a is such that the diameter 152a of the stent structure 105 has a first value. Over time, the circumferential axis of the stent structure expands outwardly as shown in FIG. 1A as 150b such that the diameter 152b of the stent structure 105 has a second value. The second value is larger than the first value, and according to various embodiments, the stent structure expands from the first value to the second value, and the second value is at least about 1.5 times the first value. In some embodiments, the stent structure increases in diameter from the initial diameter to the final (unconstrained) diameter by a factor of about 1.5 to about 5. Such embodiments may be implanted in infants and remain implanted in the patient into adulthood. In some embodiments, the stent structure increases in diameter from the initial diameter to the final (unconstrained) diameter by a factor of about 1.5 to about 3. In some embodiments, the stent structure increases in diameter from the initial diameter to the final (unconstrained) diameter by a factor of about 1.7 to about 2.8. In some embodiments, the stent structure increases in diameter from the initial diameter to the final (unconstrained) diameter by a factor of about 1.9 to about 2.6. In some embodiments, the stent structure increases in diameter from the initial diameter to the final (unconstrained) diameter by a factor of about 2.0 to about 2.4. In another embodiment, the second value is at least twice the first value. As discussed above, the stent structure 105 may be capable of expanding at least substantially by energy stored within the materials used to form the stent structure 105. The geometry or configuration of the stent structure 105 may also contribute to this capability. The factor by which the diameter increases may be selected based on the age of the patient. In addition, the force profile can be tuned or chosen based on the properties of the patient's tissue. A greater factor of expansion may be useful for a younger patient, who is expected to grow. The human heart generally stops growing in adulthood. For example, the heart of a patient who is 25 years old may not grow substantially further. On the other hand, an infant's heart is expected to grow rapidly and heart valves roughly double in size from birth to age 5 or 6.

The stent structure 105 may be designed to have any minimum (i.e., first value) diameter. Generally speaking, growth adaptive self-expanding stents are selected such that the outer diameter of the stent is greater than the inner diameter of the implantation site, which allows for the continuous outward force of the stent against the inner surface of the implantation site to both hold the stent in the deployment location and to prevent migration of the stent out of the implantation site. The design and material choices for the stent structure also impact the stent's ability to radially expand. According to at least one embodiment, the initial value for the outer diameter is at least about 4 millimeters, and according to some embodiments, the initial value for the outer diameter is in a range of about 4 millimeters to about 20 millimeters. The values included herein are selected to reflect the ability for the device to be implanted into a large population of patients with defective heart valve conditions using currently available valve assemblies.

In some embodiments, the initial outer diameter of the self-expanding stent structure is in the range of about 4 millimeters to about 20 millimeters. In some embodiments, the initial outer diameter of the self-expanding stent structure is in the range of about 5 millimeters to about 20 millimeters. In some embodiments, the initial outer diameter of the self-expanding stent structure is in the range of about 5 millimeters to about 14 millimeters. In some embodiments, the initial outer diameter of the self-expanding stent structure is in the range of about 5 millimeters to about 10 millimeters. In some embodiments, the initial outer diameter of the self-expanding stent structure is in the range of about 6 millimeters to about 14 millimeters. In some embodiments, the initial outer diameter of the self-expanding stent structure is in the range of about 7 millimeters to about 13 millimeters. In some embodiments, the initial outer diameter of the growth adaptive self-expanding stent structure is about 7 millimeters. The initial outer diameter is selected based on the age and the anatomy of the patient into which the device is to be implanted. In some embodiments, the stent structure and the plurality of restraining structures are configured for a pediatric patient. Younger patients may require a relatively small initial diameter compared to older patients. Studies of cardiovascular structure have shown that mean aortic diameter is 7 millimeters for a newborn, 14 millimeters for a six-year-old child, and 22 millimeters for an adult; mean pulmonary valve diameter is 8 millimeters for a newborn, 16 millimeters for a six-year-old child, and is 26 millimeters for an adult; mean mitral valve diameter is 10 millimeters for a newborn, 19 millimeters for a six-year-old child, and is 28 millimeters for an adult; mean aortic root diameter is 10 millimeters for a newborn, 15 millimeters for a six-year-old child, and is 30 millimeters for an adult; and mean right pulmonary artery diameter is 6 millimeters for a newborn, 12 millimeters for a six-year-old child, and is 18 millimeters for an adult.

According to one embodiment, the stent structure 105 has a COF that decreases by up to 100% when the outer diameter expands from the first value diameter value to the second value. For instance, if the first diameter value is 7 millimeters and the stent structure is designed to achieve 2$x$ expansion (such that it will expand to a fully expanded diameter of 14 millimeters) then the COF of the stent structure at the fully expanded state will be zero. This may also refer to a zero-stressed state as discussed further below.

The device may be configured such that the length 154 (i.e., as shown in FIG. 1B, the length includes the stent structure 105 and the restraining structures 155) remains essentially the same length during the expansion process. That is, the length 154 of the device remains substantially constant from the first value diameter to the second value diameter. In some embodiments, a length 154 is in a range of approximately about 5 millimeters to about 30 millimeters, and according to at least one embodiment, the length 154 may be in a range of approximately 7-30 millimeters. In another embodiment, the length 154 may be in a range of approximately 7.5-27 millimeters. In another embodiment, the length 154 may be in a range of approximately 10-25 millimeters. In another embodiment, the length 154 may be in a range of approximately 12.5-17.5 millimeters. In another embodiment, the length 154 may be in a range of approximately 7-10 millimeters. According to various aspects, the length 154 may be limited by the surrounding structures of the heart. Thus, if the device is too long, it may impede blood flow within the heart, for example, by disrupting or occluding surrounding valves or inflow/outflow vessels. Shorter devices may therefore minimize the chances of disrupting normal blood flow.

In some embodiments, the length is about 30 millimeters when the outer diameter of the stent structure is expanded to its free diameter.

Devices that have a length of up to about 15 millimeters may be useful for implanting in infants or children up to five years of age. Devices that have a length of up to about 30 millimeters may be useful for implanting in adults and children approaching adulthood.

In some embodiments, a ratio of a length of the stent structure to a diameter of the stent structure is at least 1. In some embodiments, the length is between about 1 times the final diameter and about 1.8 times the final diameter, which is the unconstrained diameter. In some embodiments, the length is between about 1.1 and about 1.7 times the final diameter. In some embodiments, the length is between about 1.15 and about 1.65 times the final diameter. In some embodiments, the length is between about 1.2 and about 1.4 times the final diameter. In some embodiments, the length is about 1.2 times the final diameter. The ratio of the length to the final diameter is selected to prevent or resist ingrowth of the patient's tissue into the stent while also minimizing blood flow obstruction. The greater the ratio of the length to the diameter, the more likely the structure is to resist ingrowth. In some embodiments, the length of the stent structure is configured to prevent ingrowth of a patient's tissue into the stent structure without disrupting or occluding blood flow.

According to a further aspect, the physical presence and the length of the stent structure 105 and restraining structures 155 may function to shield the valve assembly or otherwise provide resistance to calcification. Calcification refers to the deposit of calcium salts, especially calcium phosphate that can occur in and on materials of a medical article, such as stents, that contact a patient's bodily fluids. Calcification can affect the performance and structural integrity of the medical device, especially over extended periods of time.

The length of device may also prevent tissue ingrowth and occlusion. Without being bound by theory, it is believed that beyond a threshold length, tissue growth is unable to migrate and wrap into the inner diameter of the device, including the stent structure.

According to some embodiments, the struts 127 included in the cylindrical ring 125 may be configured to achieve a desired aspect ratio. For example, in certain embodiments a ratio of a depth 162 of the strut (see FIG. 1E) to a localized width 164 of the strut may be greater than one. This aspect ratio may be present for both the initial implanted state and the fully expanded state of the stent. This type of configuration may allow for the struts 127 to "bend" or otherwise conform to the vessel wall while still allowing for the circumference of the cylindrical ring 125 to maintain a cylindrical shape, i.e., to not buckle.

Figure 1C:
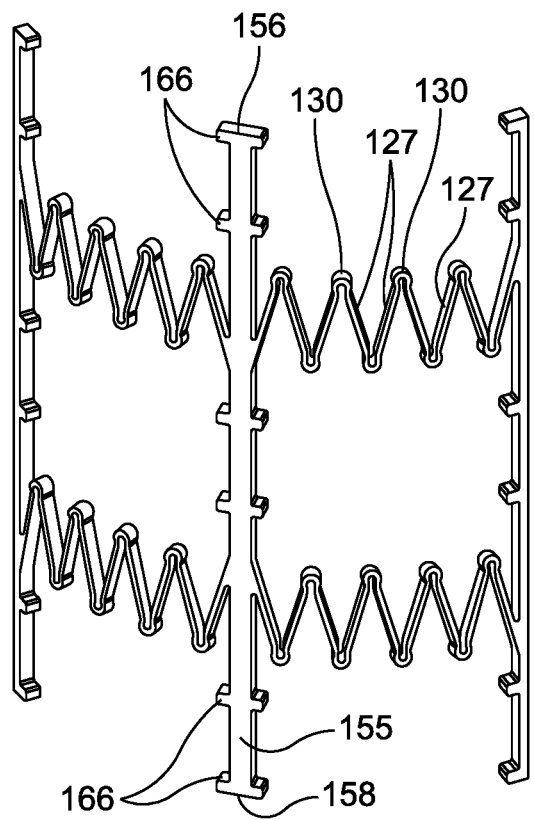
FIG. 1C is a perspective view of a segment of the stent structure as shown in FIG. 1A.
Figure 1D:
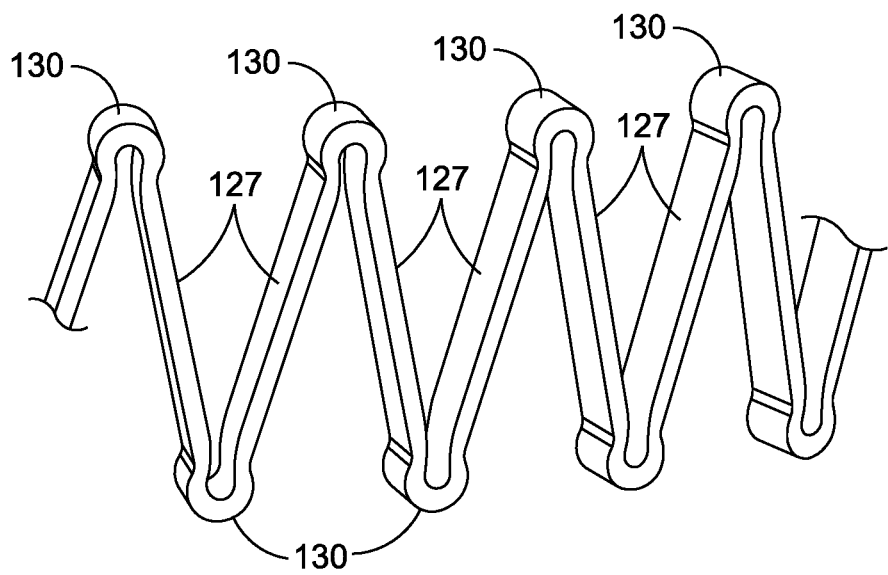
FIG. 1D is an enlarged perspective view of struts of the stent structure as shown in FIG. 1C.
Figure 1E:
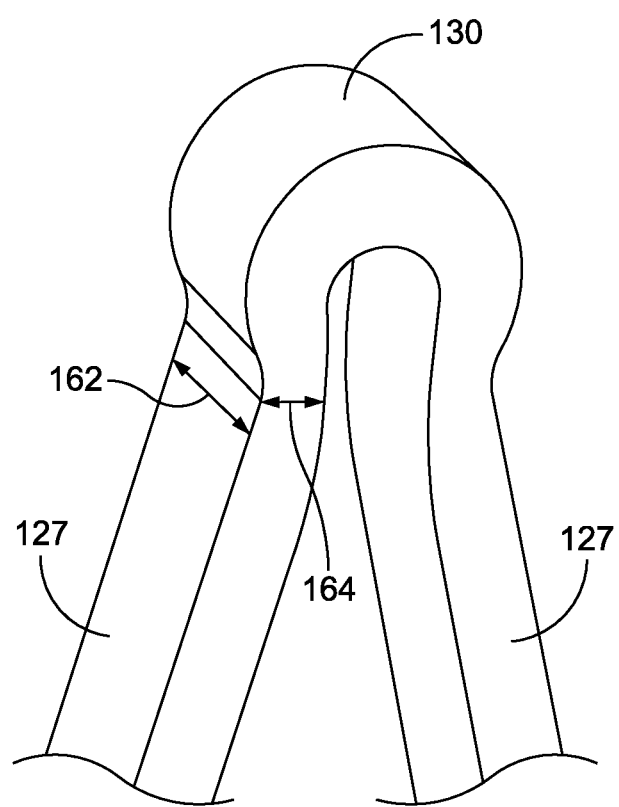
FIG. 1E is an enlarged perspective view of an apex joining two adjacent struts in the stent structure as shown in FIG. 1D.

FIGS. 1C, 1D, and 1E show enlarged perspective views of portions of the embodiment of the device of FIGS. 1A and 1B. FIG. 1E shows the localized depth of the strut at an apex and the localized width of the strut at the apex.

Because the depth 162 of the strut 127 is at least as great as a width 164 of the strut, the strut 127 preferentially bends about the apex 130 towards an adjacent strut 127. FIGS. 1C, 1D, and 1E show additional views of the struts 127. Near the apex 130, each strut 127 has a width 164 and a depth 162, as shown in FIG. 1E. While, in theory, any depth greater than the width will encourage preferential bending of a strut about the apex at least substantially towards an adjacent strut, some embodiments include a factor of safety so that the ratio of the depth to the width is greater than a number such as 1.01, 1.05, 1.1, 1.2, 1.3, or another number greater than 1. In some embodiments, the ratio of the depth 162 to the width 164 is at least 1. In some embodiments, the ratio of the depth to the width is at least 1.1. In some embodiments, the ratio of the depth to the width is at least 1.2. In certain embodiments, the thickness of the materials used in forming the stent structure may be in a range of about 50-2000 microns. For example, the thickness (depth) 162 of the strut 127 may be within this range of values. In some embodiments, the depth 162 of the strut is between about 50 microns and about 1750 microns. In some embodiments, the depth 162 of the strut is between about 50 microns and about 1500 microns. In some embodiments, the depth 162 of the strut is between about 50 microns and about 1250 microns. In some embodiments, the depth 162 of the strut is between about 50 microns and about 1000 microns. In some embodiments, the depth 162 of the strut is between about 50 microns and about 750 microns. In some embodiments, the depth 162 of the strut is between about 50 microns and about 500 microns. In some embodiments, the depth 162 of the strut is between about 75 microns and about 475 microns. In some embodiments, the depth 162 of the strut is between about 100 microns and about 450 microns. In some embodiments, the depth 162 of the strut is between about 125 microns and about 425 microns. In some embodiments, the depth 162 of the strut is between about 150 microns and about 400 microns. In some embodiments, the depth 162 of the strut is between about 175 microns and about 375 microns. In some embodiments, the depth 162 of the strut is about 300 microns. The thickness of the strut may be selected such that the strut provides some rigidity to the stent while minimizing ratio of the cross sectional area of the stent to the cross sectional area of a blood vessel or annulus.

The thickness may be selected to achieve a desired ratio of the outer diameter of the stent structure to the thickness of the strut. For example, in some embodiments, when the outer diameter of the stent structure is 5 millimeters in an uncompressed state, then the strut thickness may be 50 microns.

The thickness may be selected based on an age of the patient. A thickness of 2000 microns may be used in embodiments intended for use in adult patients. A thickness of 300 microns might be used in a younger patient. A thickness of 100 microns might be used in an adult or a child. A thickness of 30-100 microns might be used in an infant.

As noted above, the particular stent configuration shown in FIGS. 1A, and 1B is not meant to be limiting and other configurations are also within the scope of this disclosure. The configuration of the stent may be selected to achieve one or more design goals. One goal is to have a stent structure that allows for the device to remain fully operational at much smaller diameters than prosthetic heart valves that are currently available (which are designed for adults). Therefore, the stent may be configured such that the length of the stent remains substantially constant during the expansion process when the outer diameter of the stent structure expands from the first value to the second value. This results in "straight" sections of the stent structure (e.g., the restraining structures 155) disposed along the length of the stent that do not bend or otherwise flex. In addition, the stent design (and material) is configured such that stored energy is maintained in the stent upon implantation.

The stent structure may also be configured to avoid buckling and to preferentially bend at one or more locations. For instance, cylindrical rings (e.g., cylindrical ring 125) included in the stent structure may include "thinner" sections that are designed to be locations where bending may occur. The example shown in FIGS. 1A, and 1B includes cylindrical rings with struts configured such that the ratio of the thickness (depth) of the strut to the localized width of the strut is greater than one. As noted above, this allows for the strut structure to preferentially bend at these thinner sections. Another design consideration is to include enough cylindrical rings such that there is a balance in the spring constant of the stent structure. For instance, too few rings make the device too "soft" to expand in the initial state or to conform to the vessel walls, i.e., the spring constant is too low. Too many rings make the spring constant too high, which could rupture vessel walls. In cardiac applications, the number of rings and/or the strut dimensions can be tuned to match the patient's cardiac tissue, for example, so that the exerted COF is not too low or too high to adapt to the growth of the patient's cardiac tissue.

In FIG. 6, the prosthetic heart valve replacement device 100 also includes a valve assembly 170. The valve assembly 170 is disposed within the stent structure 105 and restraining structures 155 and has one or more leaflets 175 configured to permit blood flow in a first direction and impede blood flow in a second opposite direction. For instance, the arrow in FIG. 6 indicates the direction of blood flow through the leaflets 175 of the valve assembly 170. It should be noted that although the prosthetic heart valve device 100 shown in FIG. 6 includes three leaflets 175 (i.e., a tri-leaflet valve), other numbers of leaflets are also within the scope of this disclosure. For instance, the prosthetic heart valve device 100 may include two leaflets, such as in instances where the device is replacing a native mitral valve. In other embodiments, the valve assembly 170 may include one leaflet (monoleaflet configuration), and in other instances may include four or more leaflets.

The valve assembly 170 may be formed from materials known in the art, such as decellularized or cryopreserved biological material. Such materials typically include animal tissue, such as decellularized porcine aortic valve or bovine pericardium materials, or human tissue including autologous (the patient's own tissue) or allograft tissue (donor tissue). The valve assembly 170 may be coupled or otherwise attached to the restraining structures 155 and/or stent structure 105 using suturing techniques known in the art. However, according to some embodiments, other or additional valve attachment features may be included in the stent structure for purposes of attaching the valve assembly 170. The valve assembly 170 may be attached to a portion or portions of the stent that do not bend along the length of the structure and may be attached such that paravalvular leaking is minimized.

According to at least one embodiment, the stent structure 105 and plurality of restraining structures 155 may be formed from a single piece of elongated extruded tubing. These structures can be manufactured by machining a pattern into the tube using any one of a number of various known techniques, such as by laser cutting. Non-limiting representative examples of lasers that may be used to perform such a process include an excimer, carbon dioxide, and yttrium aluminum garnet (YAG) laser. In other embodiments, chemical etching may be used to form a pattern on the elongated tube.

According to one embodiment, the stent structure 105 is manufactured with a tube having a diameter that is the fully expanded value (e.g., the second value discussed above) of the stent structure. This fully expanded diameter reflects a zero-stressed state. For example, in some embodiments, the stent structure is configured to expand from an initial diameter of 7 millimeters to a final expanded diameter of 14 millimeters, so the stent structure 105 (and restraining structures 155) would be formed from a piece of tubing having a diameter of 14 millimeters. The valve assembly 170 may then be attached to the restraining structures 155, and a fixture (e.g., an iris crimper as described above) may be used to compress the device down to a diameter and/or other dimensions suitable for delivering the device to the implantation site (e.g., by catheter). Sutures (biodegradable or otherwise) may then be used to hold the device at this compressed state diameter.

According to an alternative embodiment, the stent structure 105 (and restraining structures 155) may be manufactured with a tube having a diameter that is the initial implanted diameter of the stent structure, or smaller. For instance, using the example from above, the stent structure 105 and restraining structures 155 would be formed from a piece of tubing having a diameter of 7 millimeters. The stent material may then be expanded to the desired maximum diameter (e.g., 14 millimeters) and heat-treated to ensure that the material is at a zero-stress state at the expanded position. The valve assembly 170 may then be attached to the restraining structures 155, and a fixture and sutures may be used to compress the device for delivery as described above. In either this process or the process described above, the stent material may be optionally cooled to facilitate compression for delivery.

According to some embodiments, one or more components of the prosthetic heart valve devices described herein may be further coated or integrated with one or more optional materials. For instance, the annular cuff, stent structures, restraining structures, and/or external sheath may be coated with a biological or chemical agent for promoting or resisting tissue growth or for providing resistance to calcification.

Although the examples discussed herein included valve assemblies from natural tissues, other types of valve assemblies may be used with the stent structures discussed herein. For instance, the stent structures may be used as scaffolding for tissue engineered valves. Furthermore, the stent structures disclosed herein are not limited to the use of heart valves and may be applied to other types of pediatric medical applications that involve narrowing of blood vessels, including the aorta, or other luminal passageways of the body, and may also be applied in pediatric medical devices where growth is required.

Embodiments of the growth adaptive self-expanding stent structure of the present disclosure allow for the device to be placed into a previously implanted stent structure. Because the self-expanding stent structures of the present disclosure have a chronic outward force when installed, a self-expanding stent structure of the present disclosure that is configured as a heart valve can be installed in a previously installed defective heart valve to repair and replace the defective heart valve.

Embodiments of the growth adaptive self-expanding stent structure of the present disclosure can be installed in arteries or other blood vessels, and need not include valves.

EXAMPLES

The examples that follow are intended to clarify the present invention but no claim is made as to completeness.

In the execution of the examples, an MSI R-Series Radial Expansion Force Testing apparatus (available from Machine Solutions, Inc., Flagstaff, Ariz.) was used to measure stent radial force.

Example 1: Two-Spring Design

Figure 10A:
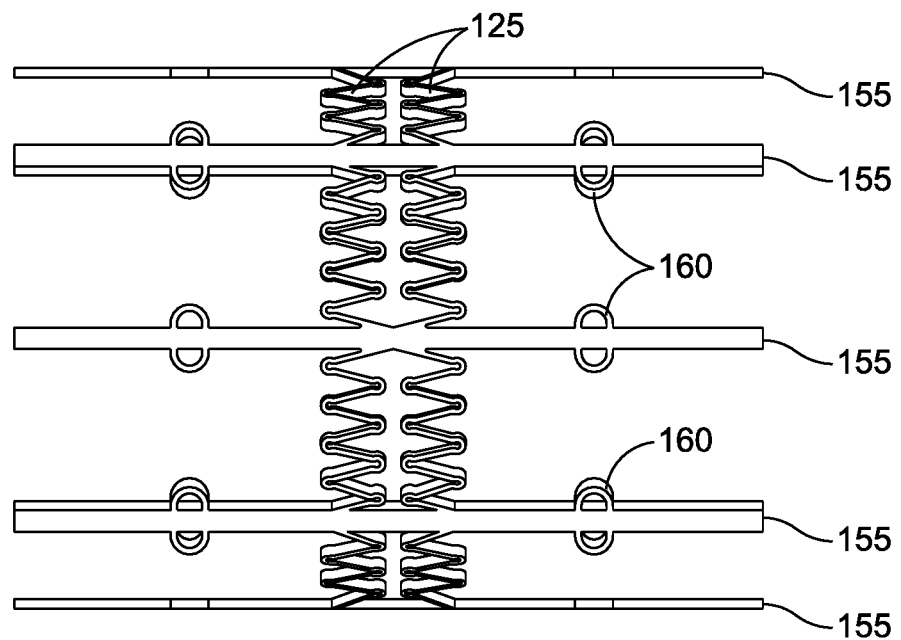
FIG. 10A is a view of a portion of a stent structure and restraining structures in accordance with one or more aspects of the invention.
Figure 10B:
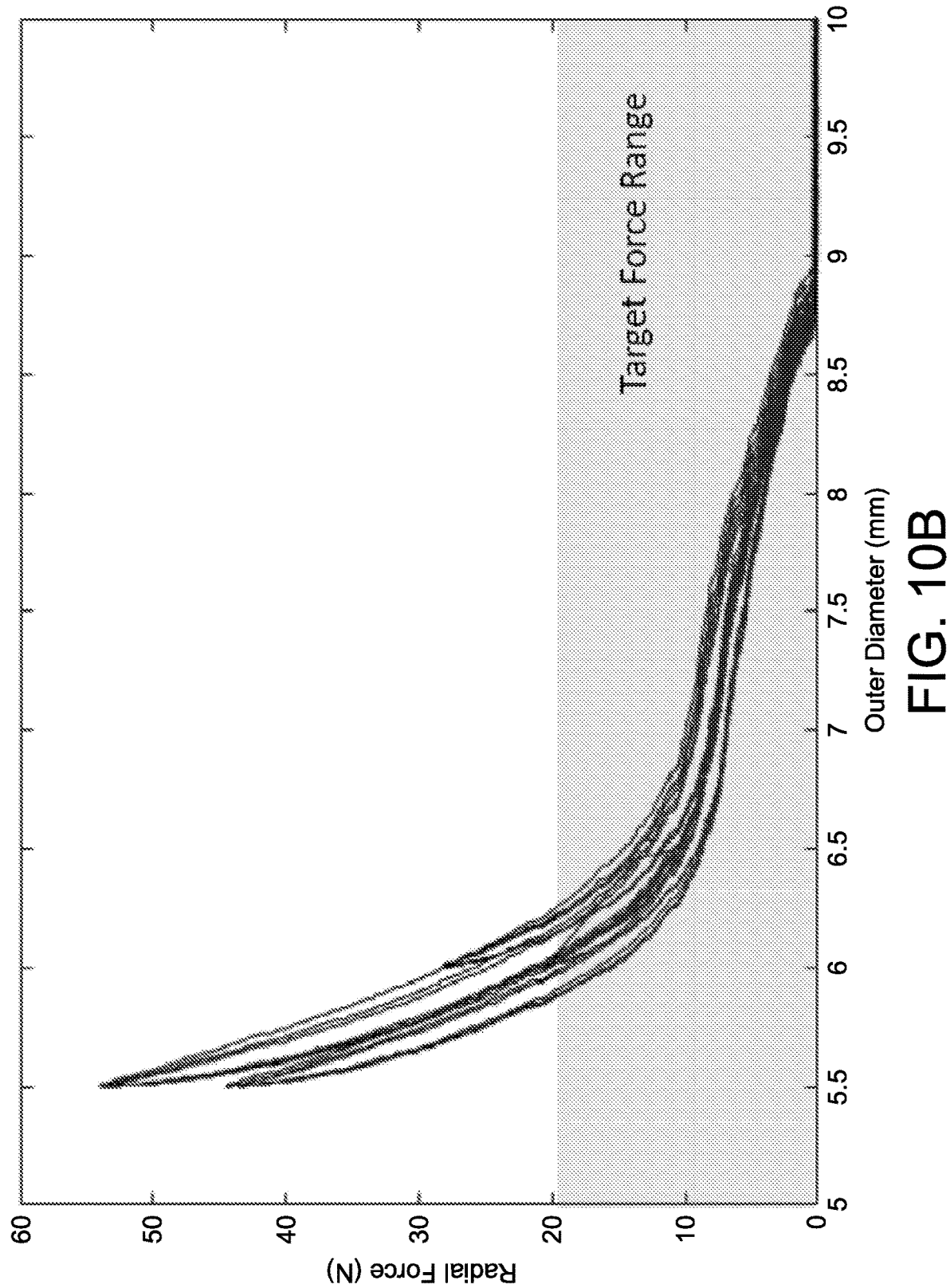
FIG. 10B is a graph plotting (outward) radial force versus outer diameter of the stent structure and restraining structures shown in FIG. 10A.

FIG. 10A is a view showing a portion of one example of a configuration for a stent structure and restraining structures manufactured from Nitinol and used for testing the stent radial force. The example device included two adjacent cylindrical rings centrally positioned along the length of the stent. According to various aspects, this configuration may be referred to as a "one spring" geometry. Three individual stent samples of three designs were each tested over multiple compression cycles, with the stent radial force results shown in FIG. 10B. The x-axis in FIG. 10B represents the compressed outer diameter of the stent (millimeters), and the y-axis represents the radial force (Newtons) applied to the stent. The results indicate that this particular two-spring design was capable of hitting the target force range (see marked section in FIG. 10B) down to an outer diameter of about 6 millimeters. The results also indicate that the load profile was consistent over multiple cycles, with small variability between the samples due to manufacturing tolerances. The force profile also agreed with models generated separately that were used in designing the stents. The models were generated using SOLIDWORKS® simulation software (available from Dassault Systemes Corp. of Waltham, Mass.).

Example 2: Six-Spring Design

Figure 11A:
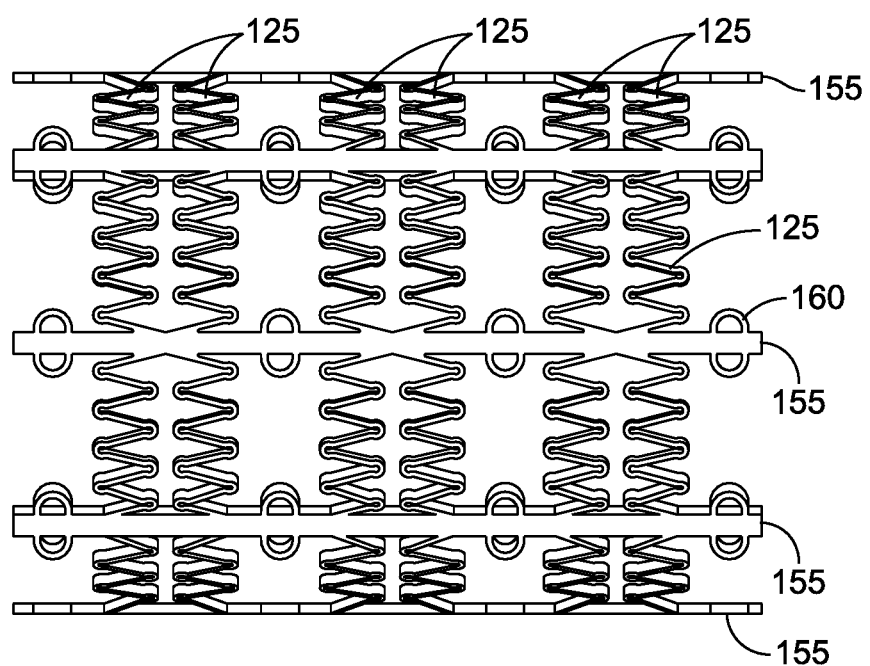
FIG. 11A is a view of a portion of a stent structure and restraining structures in accordance with one or more aspects of the invention.
Figure 11B:
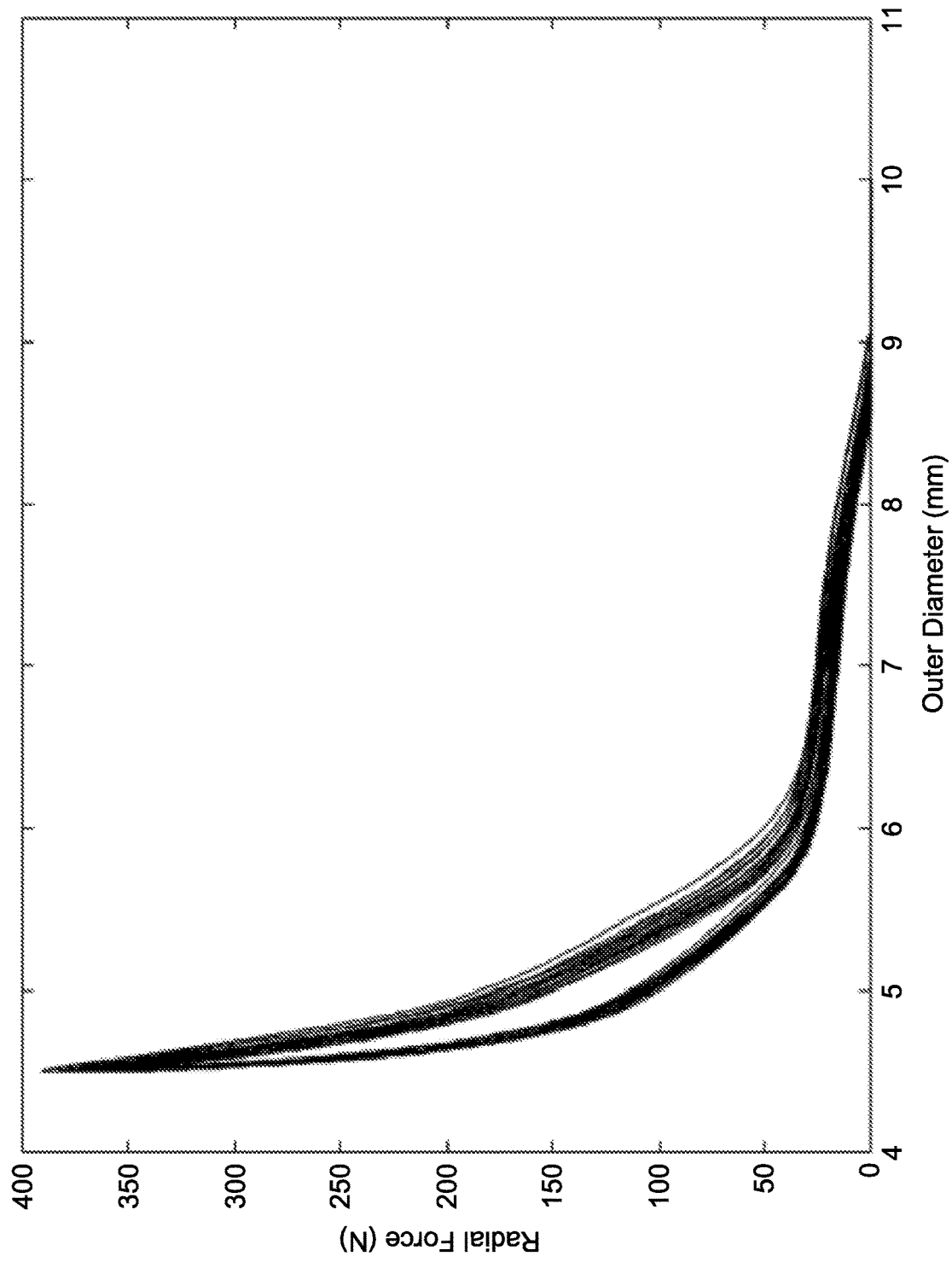
FIG. 11B is a graph plotting (outward) radial force versus outer diameter of the stent structure and restraining structures shown in FIG. 11A.

FIG. 11A is a view showing a portion of another example of a configuration for a stent structure and restraining structures that were tested in a similar manner as in Example 1, with the results shown in FIG. 11B. This design included six cylindrical rings, where two adjacent cylindrical rings are disposed at the distal end portion of the stent structure, two adjacent cylindrical rings are disposed at the central portion of the stent structure 105, and two adjacent cylindrical rings are disposed at the proximal end portion of the stent structure 105. According to various aspects, this configuration may also be referred to as a "three spring" geometry. In this instance, six stent samples were tested over multiple compression cycles. The data presented in FIG. 11B exhibits improved reproducibility per sample than the results shown in FIG. 10B of Example 1. Once normalized, the radial force applied to the stent was similar to the two-spring design of Example 1. During manufacturing of the device samples, it was found that the "stiffer" design associated with increasing the number of cylindrical rings also allowed for improved cutting accuracy, which in turn improved the cutting reproducibility between samples.

Figure 12:
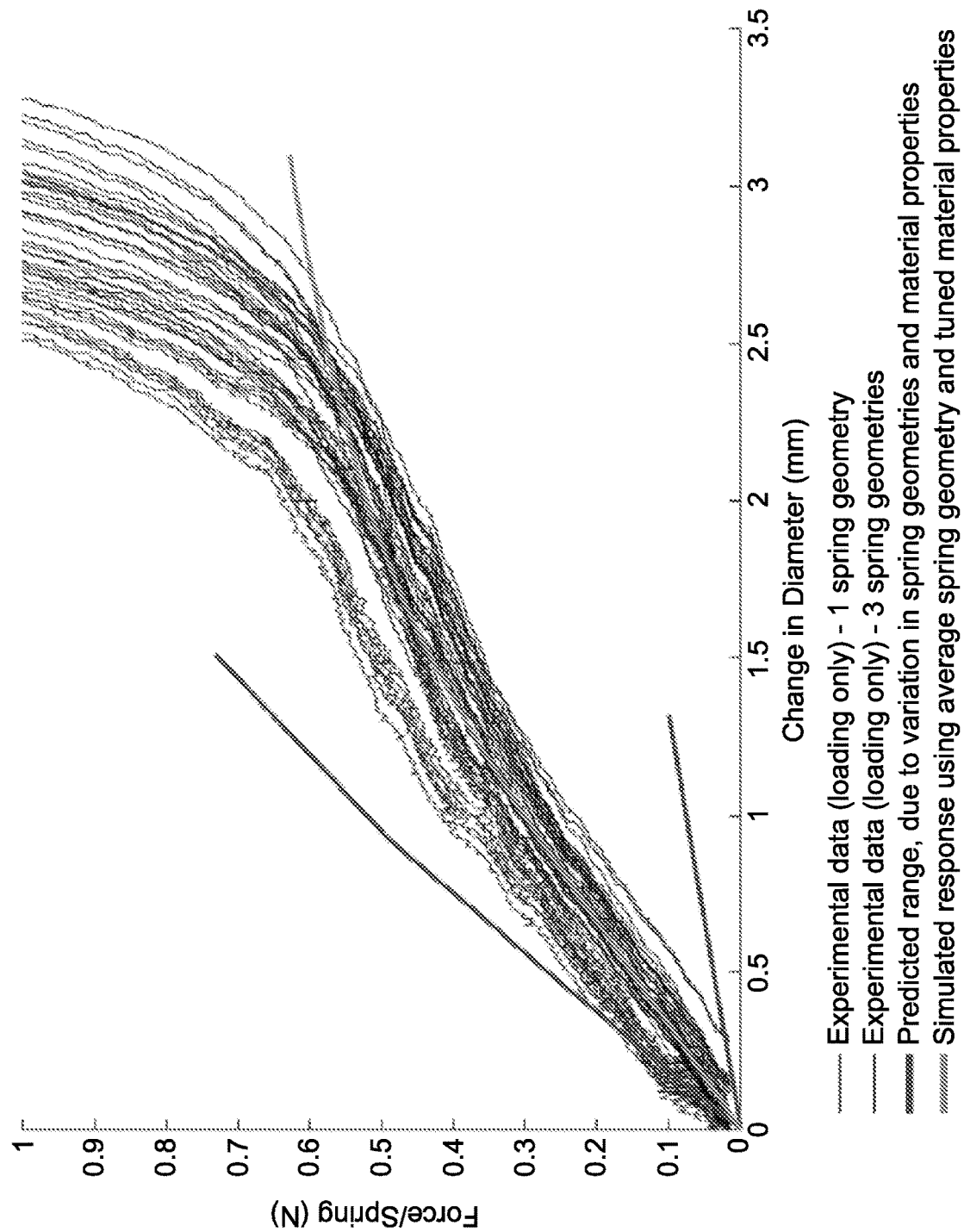
FIG. 12 is a graph that normalizes the results from FIGS. 10B and 11B.

FIG. 12 is a graph plotting normalized results from Examples 1 and 2, with the x-axis representing the change in diameter (millimeters), and the y-axis representing the normalized radial force based on the number of springs (i.e., Force/Spring) (Newtons). Also plotted are the simulated response results (from the model) and the predicted range (from the model). The variation between the predicted upper and lower ranges is due to variations in Nitinol material properties and the allowed tolerances of the manufacturing process. The results indicated that variation in width of the preferential bending locations is the strongest contributor to the spring "stiffness" as expected. Due to simplifications in constructing the model, the model also does not capture the second inflection point shown in the experimental data of FIG. 12.

Other details and illustrations associated with the prosthetic heart valve devices described herein are set forth in Appendix A and Appendix B.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A growth adaptive expandable stent for use in a heart valve device at a site, the expandable stent comprising: a stent structure having a cylindrical shape that is self-expanding in a radial direction, the stent structure having a proximal end portion, a distal end portion, and a central portion and comprising a plurality of cylindrical rings disposed along a longitudinal axis of the stent structure, each cylindrical ring of the plurality of cylindrical rings having a plurality of interconnected struts; the stent structure configured to exert a chronic outward radial force over time when implanted and in contact with the site such that an outer diameter of the stent structure expands by undergoing elastic deformation from an implanted and expanded initial diameter after delivery and implantation to a fully expanded diameter also in contact with the site that is at least 1.5 times the implanted and expanded initial diameter after implantation as the site grows,
wherein the stent structure undergoes the elastic deformation when the stent structure passively expands from the implanted and expanded initial diameter after delivery and implantation to the fully expanded diameter also in contact with the site.

2. The growth adaptive expandable stent of claim 1, wherein the chronic outward radial force is sufficient to allow the outer diameter of the stent structure to adapt to a growing shape of a biological feature in which the stent structure is implanted.

3. The growth adaptive expandable stent of claim 1, wherein the chronic outward radial force decreases by up to 100% when the outer diameter expands from the initial diameter after implantation to the fully expanded diameter.

4. The growth adaptive expandable stent of claim 1, wherein initial diameter after implantation is in a range of 4 mm to 20 mm.

5. The growth adaptive expandable stent of claim 4, wherein the initial diameter after implantation is in a range of 5 mm to 10 mm.

6. The growth adaptive expandable stent of claim 1, wherein, a ratio of a depth to a localized width of each strut allows for bending.

7. The growth adaptive expandable stent of claim 6, wherein the stent structure is configured such that a length of the stent structure remains substantially constant when the outer diameter of the stent structure expands from the initial diameter after implantation to the fully expanded diameter.

8. The growth adaptive expandable stent of claim 6, wherein the ratio of the depth of the strut to the localized width of the strut is greater than one.

9. The growth adaptive expandable stent of claim 8, wherein the depth of the strut is in a range of 50 microns to 2000 microns.

10. The growth adaptive expandable stent of claim 6, wherein a length of the stent structure is in a range of 7 mm to 30 mm when the outer diameter is the fully expanded diameter.

11. The growth adaptive expandable stent of claim 1, wherein a length of the stent structure is configured to prevent ingrowth of a patient's tissue into the stent structure without disrupting or occluding blood flow.

12. The growth adaptive expandable stent of claim 11, wherein a ratio of the length of the stent structure to the outer diameter of the stent structure is at least one.

13. The growth adaptive expandable stent of claim 1, further comprising a plurality of restraining structures disposed around the longitudinal axis of the stent structure.

14. The growth adaptive expandable stent of claim 13, wherein each restraining structure includes at least one retaining feature.

15. The growth adaptive expandable stent of claim 14, wherein at least one of the retaining features is a nubbin.

16. The growth adaptive expandable stent of claim 14, wherein at least one of the retaining features is a ring.

17. The growth adaptive expandable stent of claim 13, wherein each of the restraining structures is interspersed with the plurality of cylindrical rings.

18. The growth adaptive expandable stent of claim 13, wherein the plurality of restraining structures are interspersed with the plurality of cylindrical rings such that a pair of restraining structures are separated from one another by segments of the plurality of cylindrical rings.

19. The growth adaptive expandable stent of claim 13, wherein the stent structure and the plurality of restraining structures are formed from a material.

20. The growth adaptive expandable stent of claim 19, wherein the material is formed of a bio-compatible superelastic material.

21. The growth adaptive expandable stent of claim 13, wherein the stent structure is configured to support a valve assembly.

22. The growth adaptive expandable stent of claim 21, wherein the valve assembly has one or more leaflets and is secured to at least one of the stent structure and the plurality of restraining structures.

23. The growth adaptive expandable stent of claim 13, wherein the stent structure and the plurality of restraining structures are configured for a pediatric patient.

24. The growth adaptive expandable stent of claim 13, further comprising a sheath disposed on outer surfaces of the stent structure.

25. The growth adaptive expandable stent of claim 1, wherein the plurality of interconnected struts are configured such that two adjacent struts are connected to each other at an apex.

26. The growth adaptive expandable stent of claim 1, wherein the stent structure is configured to support a valve assembly.

27. The growth adaptive expandable stent of claim 1, further comprising a sheath disposed on outer surfaces of the stent structure.

28. The growth adaptive expandable stent of claim 1, further comprising an annular cuff secured to at least a portion of the central portion of the stent structure.

29. The growth adaptive expandable stent of claim 1, wherein the outer diameter of the stent structure expands from the initial diameter after implantation to the fully expanded diameter, and the fully expanded diameter is between 1.5 times the initial diameter after implantation and 5 times the initial diameter implantation.

30. The growth adaptive expandable stent of claim 29, wherein the outer diameter of the stent structure expands from the initial diameter after implantation to the fully expanded diameter, and the fully expanded diameter is between 1.5 times the initial diameter after implantation and 3 times the initial diameter after implantation.

31. The growth adaptive expandable stent of claim 1, wherein the outer diameter of the stent structure expands from the initial diameter after implantation to the fully expanded diameter, and the fully expanded diameter is at least twice the initial diameter after implantation.

32. The growth adaptive expandable stent of claim 31, further comprising a plurality of restraining structures disposed around a circumferential axis of the stent structure and interspersed with the plurality of cylindrical rings of the stent structure.

33. The growth adaptive expandable stent structure of claim 32, further comprising an annular cuff secured to at least a portion of the central portion of the stent structure.

34. The growth adaptive expandable stent of claim 33, further comprising a sheath disposed on outer surfaces of the stent structure.

\* \* \* \* \*